US011154205B2

(12) United States Patent
Lamata De La Orden et al.

(10) Patent No.: US 11,154,205 B2
(45) Date of Patent: Oct. 26, 2021

(54) METHOD AND SYSTEM FOR PRESSURE DROP ESTIMATION

(71) Applicant: King's College London, London (GB)

(72) Inventors: Pablo Lamata De La Orden, London (GB); David Nordsletten, London (GB); Fabrizio Donati, Horgen (CH); Nicolas Smith, Auckland (AU)

(73) Assignee: King's College London, London (GB)

( * ) Notice: Subject to any disclaimer, the term of this patent is extended or adjusted under 35 U.S.C. 154(b) by 560 days.

(21) Appl. No.: 16/085,258

(22) PCT Filed: Mar. 14, 2017

(86) PCT No.: PCT/GB2017/005694
§ 371 (c)(1),
(2) Date: Sep. 14, 2018

(87) PCT Pub. No.: WO2017/158343
PCT Pub. Date: Sep. 21, 2017

(65) Prior Publication Data
US 2019/0082970 A1 Mar. 21, 2019

(30) Foreign Application Priority Data
Mar. 15, 2016 (GB) .................... 1604412

(51) Int. Cl.
*A61B 5/021* (2006.01)
*A61B 5/00* (2006.01)
(Continued)

(52) U.S. Cl.
CPC ............ *A61B 5/021* (2013.01); *A61B 5/0263* (2013.01); *A61B 5/055* (2013.01); *A61B 5/7242* (2013.01);
(Continued)

(58) Field of Classification Search
CPC ........... A61B 5/021; A61B 5/00; A61B 5/026; A61B 5/055; A61B 8/08; A61B 8/488;
(Continued)

(56) References Cited

U.S. PATENT DOCUMENTS

2013/0090555 A1 4/2013 Kassab
2013/0243294 A1* 9/2013 Ralovich ............... G06T 7/0012
382/131
(Continued)

FOREIGN PATENT DOCUMENTS

EP 2633815 A1 9/2013
GB 2479340 A 10/2011
WO 2017158343 A1 9/2017

OTHER PUBLICATIONS

Mihalef V. et al. (2014) Model-Based Estimation of 4D Relative Pressure Map from 4D Flow MR Images. In: Statistical Atlases and Computational Models of the Heart. Imaging and Modelling Challenges. STACOM 2013. Lecture Notes in Computer Science, vol. 8330. Springer, Berlin, Heidelberg. pp. 236-243 (Year: 2014).*
(Continued)

*Primary Examiner* — Eric J Messersmith
(74) *Attorney, Agent, or Firm* — Banner & Witcoff, Ltd.

(57) ABSTRACT

Embodiments and aspects described herein provide a method of determining pressure difference across a tube arising from fluid flow within the tube, comprising: obtaining three-dimensional time dependent fluid velocity data at a plurality of points along the tube; processing the three-dimensional time dependent fluid velocity data to determine: i) a flow rate (Q) of the fluid through the tube; ii) the kinetic energy (K) of the fluid flow through the tube; iii) an advective energy rate (A) of the fluid flow through the tube; and iv) a viscous dissipation rate (V) pertaining to the fluid flow; and calculating the pressure difference in dependence on all of the flow rate (Q), kinetic energy (K), advective
(Continued)

Simplified Bernoulli

Corrected Bernoulli

Full WERP

Complete Advective WERP

Simplified Advective WERP $\Delta P_{SB} = -4V^2_{MAX}$   $\Delta P_{CB} = -4(V^2_{MAX} - V^2_{PROX})$   $\Delta P_W = -\dfrac{\partial K/\partial t + A + V}{Q}$   $\Delta P_{CAW} = -\dfrac{A_{INLET} + A_{OUTLET}}{Q}$   $\Delta P_{SAW} = -\dfrac{A_{OUTLET}}{Q}$ energy rate (A), and viscous dissipation rate (V). Further embodiments and aspects are also described.

19 Claims, 18 Drawing Sheets

(51) Int. Cl.
    *A61B 5/026*      (2006.01)
    *A61B 8/08*      (2006.01)
    *A61B 8/06*      (2006.01)
    *A61B 5/055*      (2006.01)
    *A61B 8/04*      (2006.01)

(52) U.S. Cl.
    CPC ............... *A61B 8/04* (2013.01); *A61B 8/06* (2013.01); *A61B 8/488* (2013.01); *A61B 8/5223* (2013.01); *A61B 2576/023* (2013.01)

(58) Field of Classification Search
    CPC ....... A61B 5/0263; A61B 8/5223; A61B 8/06; A61B 5/7242; A61B 8/04; A61B 2576/023
    See application file for complete search history.

(56) References Cited

U.S. PATENT DOCUMENTS

2015/0063649 A1*    3/2015    Mihalef ................... G06T 7/20
                                                                   382/107
2015/0268039 A1    9/2015    Tu et al.
2016/0228190 A1*    8/2016    Georgescu ............. A61B 8/065

OTHER PUBLICATIONS

Donati, Fabrizio & Figueroa, Carlos & Smith, Nicolas & Lamata, Pablo & Nordsletten, David. (2014). Non-Invasive Relative Pressure Estimates from Fluid Energy using PCMRI. 10.13140/RG.2.2.28773.19685. Sep. 2014 (Year: 2014).*

Wendell, et al. "Including aortic valve morphology in computational fluid dynamics simulations: Initial findings and application to aortic coarctation," Medical Engineering & Physics 35 (2013) 723-735 (Year: 2013).*

Fabrizio, Donati et al: "Non-invasive pressure difference estimation from PC-MRI using the work-energy equation", Medical Image Analysis, vol. 26, No. 1, Sep. 8, 2015 (Sep. 8, 2015), pp. 159-172, XP055371638, GB.

Gardner RM. Direct arterial pressure monitoring. Curr Anaesth Crit Care. 1990;1:239-246.

Niederberger J, Schima H, Maurer G, Baumgartner H. Importance of pressure recovery for the assessment of aortic stenosis by Doppler ultrasound. Role of aortic size, aortic valve area, and direction of the stenotic jet in vitro. Circulation. 1996;94:1934-1940.

Lee TC, Kashyap RL, Chu CN. Building Skeleton Models via 3-D Medial Surface Axis Thinning Algorithms. CVGIP Graph. Model. Image Process. 1994;56:462-478.

Falahatpisheh A, Rickers C, Gabbert D, Heng EL, Stalder A, Kramer H-H, Kilner PJ, Kheradvar A. Simplified Bernoulli's method significantly underestimates pulmonary transvalvular pressure drop. J Magn Reson Imaging. 2015;n/a-n/a.

International Search Report and WO for PCT/GB2017/050694: dated May 18, 2017.

Computing in Cardiology, Jul. 9, 2014,RANDLES et al., Analysis of pressure gradient across aortic stenosis with masssively parallel computational simulations, pp. 217-220.

* cited by examiner

FIELD EVALUATION M(V)

(a)

(b)

FIELD DERIVATIVE EVALUATION D(V)

(c)

(d)

METHOD AND SYSTEM FOR PRESSURE DROP ESTIMATION

CROSS-REFERENCE TO RELATED APPLICATIONS

This application is a U.S. National Stage application under 35 U.S.C. § 371 of International Application PCT/GB17/50694 (published as WO 2017/158343 A1), filed Mar. 14, 2017, which claims the benefit of priority to Application GB 1604412.5, filed Mar. 15, 2016.

Benefit of the filing date of each of these prior applications is hereby claimed. Each of these prior applications is hereby incorporated by reference in its entirety.

TECHNICAL FIELD

The present invention relates to a method and system for estimating the pressure drop through a vessel, and in particular embodiments to the estimation of blood pressure drop through a blood vessel based on measurements of velocity obtained from various medical imaging modalities.

BACKGROUND TO THE INVENTION AND PRIOR ART

Pressure drops or differences (also referred as pressure gradients in some clinical literature) measured over vascular segments are widely used clinically as biomarkers for a number of cardiovascular disorders (Baumgartner, Hung, Bermejo, Chambers, Evangelista, Griffin, Jung, Otto, Pellikka, Quiñones, 2009, Sawaya, Stewart, Babaliaros, 2012 and Vahanian, Baumgartner, Bax, Butchart, Dion, Filippatos, Flachskampf, Hall, Jung, Kasprzak, Nataf, Tornos, Torracca, Wenink, 2007). A well-known example is aortic coarctation (CoA), where the pressure drop is used as a diagnostic metric to risk stratify patients undergoing surgery (Jenkins, Ward, 1999 and Oshinski, Parks, Markou, Bergman, Larson, Ku, Mukundan, Pettigrew, 1997) and to evaluate patients after stenting (Tan et al., 2005). Other examples of pressure based metrics in the clinic include the transvalvular drop—an accepted metric to classify the severity of aortic valve stenosis (Baumgartner, Hung, Bermejo, Chambers, Evangelista, Griffin, Jung, Otto, Pellikka, Quiñones, 2009, De Bruyne, Manoharan, Pijls, Verhamme, Madaric, Bartunek, Vanderheyden, Heyndrickx, 2006 and Feldman, 2006), the Left-Ventricle Outflow Tract (LVOT) pressure drop—used to define the guidelines for the treatment of Hypertrophic Cardiomyopathy (HCM) (Gersh et al., 2011), and the transstenotic pressure difference in the coronary artery—used to quantify the Fractional Flow Reserve (FFR) (Deng et al., 2014).

The measurement of pressure differences in current clinical guidelines is based on catheter measurements (Feldman, 2006 and Konecny, Khanna, Novak, Jama, Zawadowski, Orban, Pressman, Bukartyk, Kara, Cetta, Borlaug, Somers, Reeder, 2014) or echocardiographic Doppler recordings (Bach, 2010, Firstenberg, Greenberg, Smedira, Prior, Scalia, Thomas, Garcia, Michael, Smedira, Thomas, 2000, Fyfe, Currie, Seward, Tajik, Reeder, Mair, Hagler, 1984, Labovitz, Ferrara, Kern, Bryg, Mrosek, Williams, 1986 and Zhang, Nitter-Hauge, 1985). Pressure catheterization has seen significant improvement in terms of probe sensitivity (de Vecchi, Clough, Gaddum, Rutten, Lamata, Schaeffter, Nordsletten, Smith, 2014, Garcia, Carrozza, 2007 and Iwasaki, Kusachi, 2009) and surgical administration, making it the gold standard in pressure drop measurement. However, despite its advantages, application of pressure catheterization is limited to specific cohorts of patients due to its intrinsic invasiveness and associated risks and cost. To broaden the base of patients who could benefit from these assessments, non-invasive evaluation using Doppler echocardiography was developed. Applying this modality, the pressure difference is estimated from the peak velocity magnitude acquired along the direction of an ultrasound beam through a simplified Bernoulli formulation (Hatle, Brubakk, Tromsdal, Angelsen, 1978 and Oshinski, Parks, Markou, Bergman, Larson, Ku, Mukundan, Pettigrew, 1997). While useful for patient stratification, the accuracy of this approach is limited by operator dependence and the mathematical assumptions, which rely on neglecting transient effects and viscous losses on the flow (Holen, Simonsen, 1979, Laske, Jenni, Maloigne, Vassalli, Bertel, Turina, 1996 and Zhang, Nitter-Hauge, 1985).

Working with the same Doppler Echocardiography data, pressure differences estimation has been improved by the use of Euler equations, as used in the characterisation of diastolic performance (Bermejo, Antoranz, Yotti, Moreno, Garcia-Fernandez, 2001, Greenberg, Vandervoort, Firstenberg, Garcia, Thomas, Neil, Firstenberg, 2001 and Yotti, Bermejo, Antoranz, Rojo-Álvarez, Allue, Silva, Desco, Moreno, García-Fernández, 2004). This approach benefits from high temporal resolution of the data, but neglects the effects related to advective acceleration out of the line of insonation as well as to viscous dissipation. Doppler acquisitions are also dependent on the ability of the operator to detect the blood flow direction. All these factors have motivated continued research to improve robustness, accuracy and operator independence.

Recent advances in Magnetic Resonance Imaging (MRI) and Echocardiography have allowed the acquisition of velocity data in three-dimensional space and time (Deng, Fan, Xie, He, Natsuaki, Jin, Bi, An, Liu, Zhang, Fan, Li, 2014, Herment, Besson, Frouin, 2008, Markl, Wallis, Brendecke, Simon, Frydrychowicz, Harloff, 2010 and Nielsen, Powell, Gauvreau, Marcus, Prakash, Geva, 2005). Ongoing research efforts have produced a number of different techniques to estimate pressure differences using these images. Particularly, Four Dimensional Phase-Contrast MRI (4D PC-MRI) data enables the solution of the Poisson Pressure Equation (PPE), where pressure is derived explicitly as a function of the acquired velocity field (Bock, Frydrychowicz, Lorenz, Hirtler, Barker, Johnson, Arnold, Burkhardt, Hennig, Markl, 2011 and Krittian, Lamata, Michler, Nordsletten, Bock, Bradley, Pitcher, Kilner, Markl, Smith, 2012), allowing the estimation of the convective effects in all spatial directions and the contribution of viscous dissipation (Lamata et al., 2014). This approach has been successfully applied for the estimation of the pressure in aortic coarctation (Riesenkampff et al., 2014). Building on these data-driven methods, reconstruction of the velocity field at the vascular walls (Donati et al., 2014) has been proposed to improve the accuracy of the computation of the viscous effects, and data-assimilation techniques attempted to overcome the limitations of data acquisition with physically-based simulations (de Hoon et al., 2014).

An alternative approach to estimate pressure differences in the vascular anatomy is based on 3D Computational Fluid Dynamics (CFD) simulations (Kim, Vignon-Clementel, Coogan, Figueroa, Jansen, Taylor, 2010, LaDisa, Figueroa, Vignon-Clementel, Jin Kim, Xiao, Ellwein, Chan, Feinstein, Taylor, 2011, Sankaran, 2012 and Vignon-Clementel, Figueroa, Jansen, Taylor, 2010). In this case, patient specific geometric models are reconstructed from images such as computed tomography angiography and velocity boundary conditions are defined from flow measurements. Consequently, pressure and velocity are simulated over the cardiovascular model (Coogan, Humphrey, Figueroa, 2013 and Xiao, Alastruey, Figueroa, 2014), providing detailed metrics of flow, pressure differences, wall shear stress, amongst others. While providing these detailed metrics, forward cardiovascular modeling based on CFD requires robust multi-scale approaches for boundary conditions (Formaggia, Gerbeau, Nobile, Quarteroni, 2002, Gresho, Sani, 1987 and Vignon-Clementel, Figueroa, Jansen, Taylor, 2006), accurate anatomical definition and the solution of expensive, parallel simulations in a computer cluster

SUMMARY OF THE INVENTION

In one embodiment described herein we present a non-invasive semi-automatic method for the estimation of pressure differences based on the work-energy principle, namely the Work-Energy Relative Pressure (WERP) method. The arrangement has benefits of simplicity and computational efficiency, requiring integrations and computations that can be executed directly from the image acquired using 4D PC-MRI or Echocardiography (ECG). Introducing the mathematics behind the method, we detail its application for cardiovascular flow data. In the first accompanying appendix we describe tests of the method on a series of in silico test cases with progressively increasing complexity, evaluating robustness to segmentation variability and noise. Subsequently, the proposed method is thoroughly compared with other available methods on an in silico CFD solution. Finally, the satisfactory performance of the method is demonstrated on 4D PC-MRI acquisitions on a cohort of 9 healthy patients, by comparing estimated aortic pressure differences to previously reported results obtained with a PPE-based approach (Lamata et al., 2014).

In further embodiments based on the above described embodiment, we also describe two simplified approaches for pressure estimation, which require less information than the WERP method, and as a consequence can be used with data from other imaging modalities other than 4D PC-MRI, and in particular using 3D Doppler echocardiographic (ECG) images or 2D PC-MRI for the first simplified approach, or even Doppler ECG images from conventional 2D probes for the second simplified approach. The techniques can also be applied to velocity fields reconstructed from compound ECG, or from speckle/contrast tracking in ultrafast ECG. As 2D and 3D ECG imaging is much more prevalent in clinical settings than 4D PC-MRI, the simplified approaches have significantly more widespread application than the full WERP approach.

In view of the above, from a first aspect there is provided a method of determining pressure difference across a tube arising from fluid flow within the tube, comprising: obtaining three-dimensional time dependent fluid velocity data at a plurality of points along the tube; processing the three-dimensional time dependent fluid velocity data to determine: i) a flow rate (Q) of the fluid through the tube; ii) the kinetic energy (K) of the fluid flow through the tube; iii) an advective energy rate (A) of the fluid flow through the tube; and iv) a viscous dissipation rate (V) pertaining to the fluid flow; and calculating the pressure difference in dependence on all of the flow rate (Q), kinetic energy (K), advective energy rate (A), and viscous dissipation rate (V).

From another aspect there is also provided a method of determining pressure difference across a tube arising from fluid flow within the tube, comprising: obtaining fluid velocity data at the inlet and outlet planes of the tube; processing the fluid velocity data to determine: i) a flow rate (Q) of the fluid through the tube; and ii) an advective energy rate (A) of the fluid flow through the tube; and calculating the pressure difference in dependence on both of the flow rate (Q), and the advective energy rate (A), without considering a viscous dissipation rate (V) and the kinetic energy (K) of the fluid flow through the tube.

A further aspect provides a method of determining pressure difference across a tube arising from fluid flow within the tube, comprising: obtaining fluid velocity data only at the outlet of the tube, (which is a valid assumption when the velocities at the inlet are negligible compared to outlet velocities); processing the fluid velocity data to determine: i) a flow rate (Q) of the fluid through the tube; and ii) an advective energy rate (A) of the fluid flow through the tube but only considering the outlet; and calculating the pressure difference in dependence on both of the flow rate (Q), and the advective energy rate (A), without considering a viscous dissipation rate (V) and the kinetic energy (K) of the fluid flow through the tube.

A further aspect provides a set of methods of determining the advective energy rate (A) in all previous embodiments adapted to the resolution and availability of data depending on the imaging modality. The methods comprise: (a) a method that uses data from the complete cross-section of the inlet or outlet plane of the tube, and each data point is the complete 3D velocity vector as originated by 4D PCMRI; (b) a method that uses data from the complete cross-section of the inlet or outlet plane of the tube, and each data point is a projector of the 3D velocity vector in the direction of the insonation line, as originated by 3D ECG; (c) a method that uses data from only a line of the cross-section of the inlet or outlet plan of the tube, and each data point is a projection of the 3D velocity vector in the direction of the insonation line, as originated by 2D ECG; (d) a method that uses data from a combination of lines of the cross-section of the inlet or outlet plane of the tube, and each data point is a projection of the 3D velocity vector in the direction of the insonation line, as originated by multiple 2D ECG acquisitions.

Finally, from another aspect, some embodiments of the invention also provide a method of determining pressure difference across a tube arising from fluid flow within the tube, comprising: obtaining three-dimensional time dependent fluid velocity data at a plurality of points along the tube; segmenting a domain of interest in the tube for which flow information therethrough is desired defining a flow vector field w through the segmented domain, being a field that is divergence free and that has null values in the lateral walls of the tube; processing the flow vector field w and the three-dimensional time dependent fluid velocity data to determine: i) a flow rate (Qw) of the flow vector field w; ii) a surrogate kinetic energy (Kw) of the fluid flow through the tube; iii) a surrogate advective energy rate (Aw) of the fluid flow through the tube; and iv) a surrogate viscous dissipation rate (Vw) pertaining to the fluid flow; and calculating the pressure difference in dependence on all of the flow rate (Qw), and surrogates of kinetic energy (Kw), advective energy rate (Aw), and viscous dissipation rate (Vw).

Further features of embodiments of the invention will be apparent from the appended claims.

BRIEF DESCRIPTION OF THE DRAWINGS

Embodiments of the invention will now be further described by way of example only and with reference to the accompanying drawings, wherein like reference numerals refer to like parts, and wherein.

DESCRIPTION OF THE EMBODIMENTS

Figure 12:
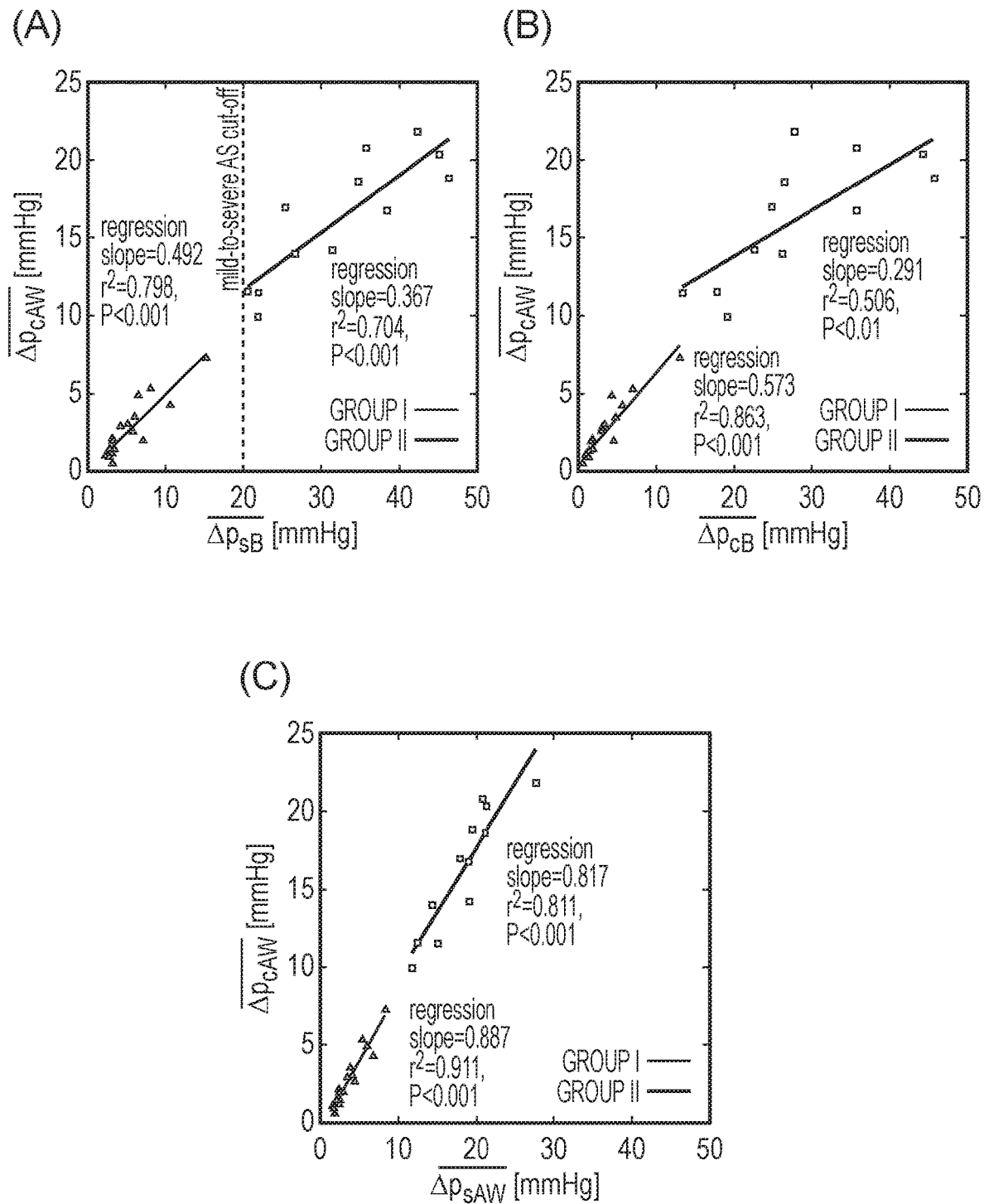

Embodiments of the invention will now be described. Three embodiments will be described, the first embodiment relating to pressure drop estimation in the heart using the full WERP approach which models the pressure drop in detail over a whole length of the blood vessel of interest, the second embodiment relating to the so-called "complete Advective WERP" approach which models the pressure drop via measurements at the inlet and outlet of the vessel only, and the third embodiment being a so-called "simplified advective WERP" method, which makes use of measurements at the outlet of the vessel only. FIG. 2 illustrates the measurements and the computations required for each approach, whereas FIG. 12 gives further details of the anatomical regions of interest (particularly used in the second and third embodiments) (see FIG. 1(A)), and the different data that can be obtained from different imaging modalities (FIG. 1(B)).

Figure 1:
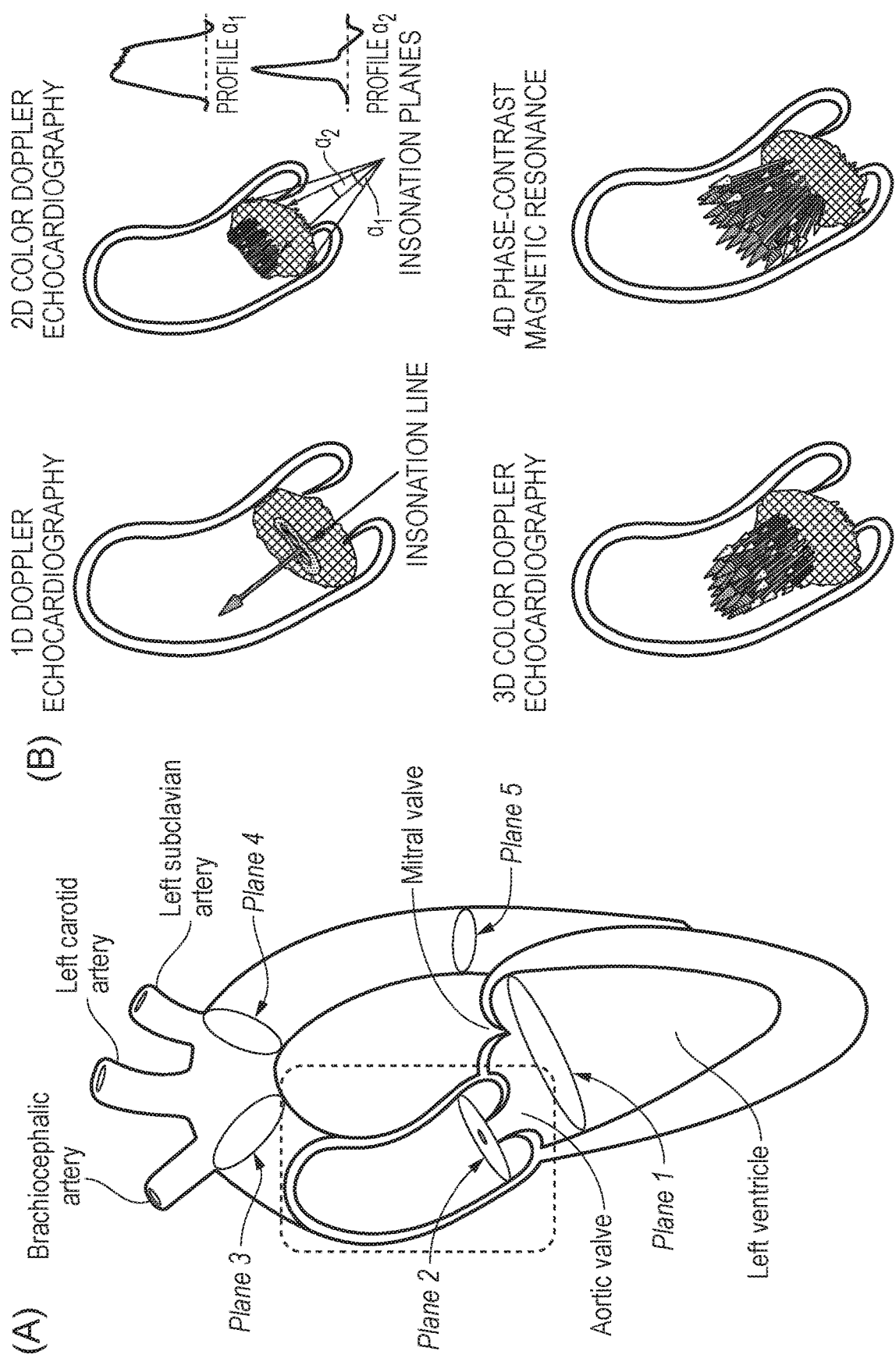
FIG. 1 is a set of diagrams illustrating various uses of embodiments of the invention.
Figure 2:
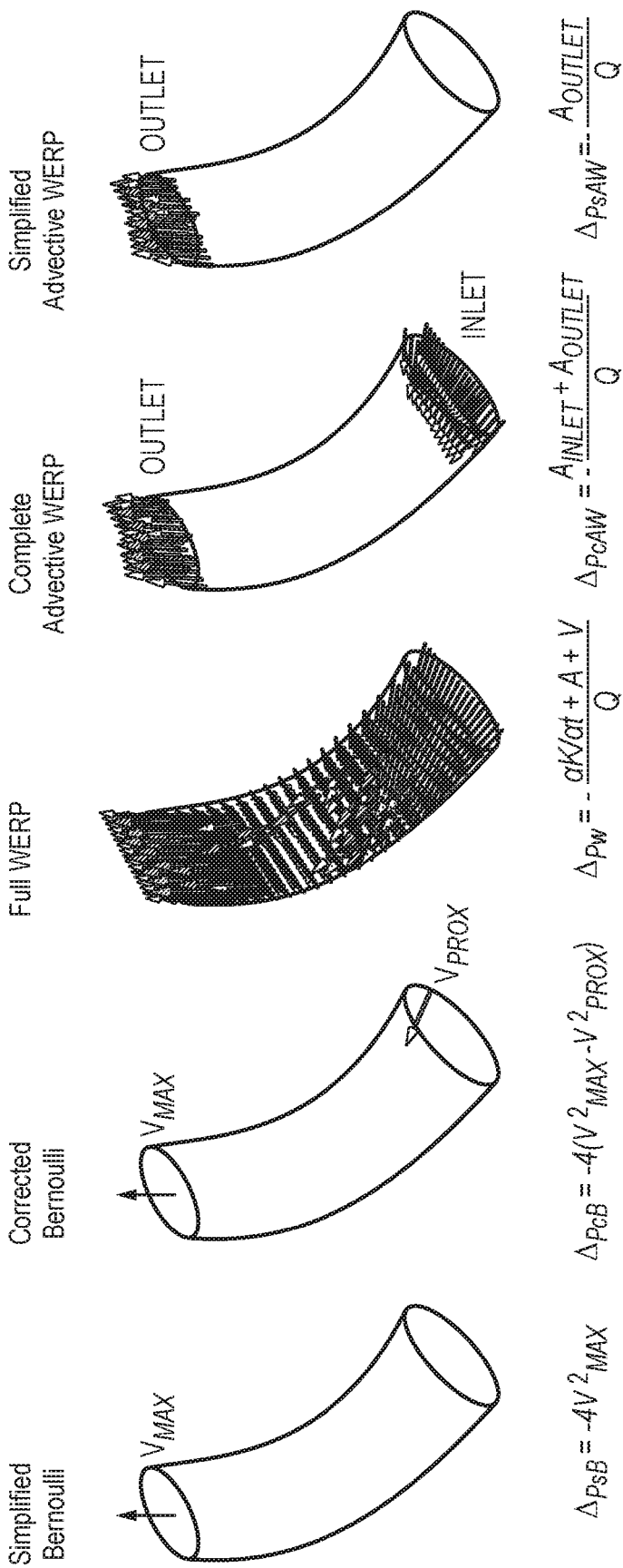
FIG. 2 is a set of diagrams illustrating measurements collected by embodiments of the invention, and associated mathematical formula for the computation of the pressure drop.

In FIG. 1 (A) the definition of anatomical regions where the pressure drops are computed are as follows: Trans Valvular Region (TVR): from the left ventricle outflow tract (LVOT) (Plane 1) to the vena contract (VC) (Plane 2); Ascending Aorta Region (AAR): from the VC to the brachiocephalic artery (Plane 3); Descending Aorta Region (DAR) from the left subclavian artery (Plane 4) to a plane at the same height of the aortic valve plane (Plane 5).

In FIG. 1(B) is shown schematics of the velocity field at the VC acquired at peak systole with different techniques and increasing level of data availability, as follows. Top left: A single velocity value is obtained from continuous 1D Doppler. Top right: A 1D velocity profile along a plane of insonation is available from a 2D color Doppler. Bottom left: A complete 2D velocity profile is available from a 3D color Doppler. Bottom right: The complete velocity vector field over the entire plane, and not simply its projection along the insonation line, is available from 4D PC-MRI.

With respect to the first embodiment, referred to as the full WERP approach, this can be summarised as follows: Given a fluid through a tubular structure, the computation of the difference of pressure between the inlet and outlet is given by the work-energy relative pressure (WERP) method, which is derived from the work-energy principle obtained from the Navier Stokes equation, and computes the pressure difference as an addition of three rates of energy transfer (kinetic, advective and viscous) divided by the net flow through the tube. The kinetic term integrates the rate of temporal change in kinetic energy of all particles within the tubular domain. The second term describes the rate of energy transfer due to the physical movement of a fluid in and out of the domain. And the third term describes the energy dissipated due to viscous friction of the fluid.

With respect to the second embodiment, referred to as the complete advective WERP approach, this can be summarised thus: Given a fluid through a tubular structure, the computation of the difference of pressure between the inlet and outlet is given by the advective WERP equation, which is a simplification of the WERP equation by only taking one of the three additive terms of energy, the advective term. In more detail, this component of energy neglects the contribution of the advected energy from the lateral walls, as velocities perpendicular to the wall are small in the near-wall regions, and the computation of the pressure difference reduces to the integral of the advected energy rate at the inlet and outlet planes of the tubular structure.

Finally, with respect to the third embodiment, being the simplified advective WERP approach, the following is a summary thereof: Given a fluid through a tubular structure, the computation of the difference of pressure between the inlet and outlet is given by the simplified advective WERP equation, which is a simplification of the complete advective WERP equation by only taking the contribution of either the inlet or outlet planes of the tubular domain. The assumption here is that the integral of advected energy rate at the other end of the tubular domain is negligible.

First Embodiment: Full WERP

2. Methods

Starting from the work-energy principle, we derive the formula for the pressure difference over a vascular segment (Section 2.1). Subsequently, we detail its discrete formulation (Section 2.2) and pre-processing steps (Section 2.3) required to work with 4D PC-MRI data.

2.1. Pressure Difference from Fluid Work Energy

Pressure differences in a fluid system are related to the kinematics of the flow field. This relationship is described by the well-known Navier-Stokes equations where, in the absence of gravity, variations in pressure are balanced by fluid accelerations and viscous stresses. Using the conservation of mass and momentum for closed systems, the work-energy for an incompressible isothermal Newtonian fluid over a Region Of Interest (ROI) ($\Omega$) with boundary $\Gamma$ yields, $$\underbrace{\frac{\rho}{2}\frac{\partial}{\partial t}\int_\Omega (v \cdot v)dx}_{\frac{\partial}{\partial t}K_e} + \underbrace{\frac{\rho}{2}\int_\Gamma |v|^2(v \cdot n)dx}_{A_e} +$$

$$\underbrace{\int_\Gamma pv \cdot n dx}_{H(p)} - \underbrace{\int_\Gamma \mu[D(v) \cdot n] \cdot v dx}_{S_e} + \underbrace{\frac{\mu}{2}\int_\Omega D(v):D(v)dx}_{V_e} = 0,$$

where v represents the velocity, p the pressure, n is the normal vector on Γ, D(•)=[∇(•)+∇T(•)], and ρ and μ as the fluid density and dynamic viscosity. Here, $$\frac{\partial}{\partial t}K_e$$

is the temporal derivative of the kinetic energy within Ω, $A_e$ the advected energy rate describing the energy transfer due to the physical movement of a fluid in and out of Ω and $V_e$ is the rate of viscous dissipation. H(p) and $S_e$ represent energy inputs to the fluid system, the hydraulic power and the shear energy rate, respectively. Here we assume that the boundary of the Ω can be written as Γ=Γ$_i$∪Γ$_o$∪Γ$_w$, where i, o and w indicate contributions from the vessel inlet, outlet and walls surface. The mathematical details behind the work-energy principle derivation can be found in our published paper Donati et al *Non-invasive pressure difference estimation from PC-MRI using the work-energy equation* Medical Image Analysis, Vol. 26, pp. 159-172, December 2015, the entire contents of which necessary for understanding the present embodiments being incorporated herein by reference.

Starting from this work-energy balance, as a first approximation, we ignore the contribution to the advected energy $A_e$ from the lateral walls Γ$_w$, as velocities are small in the near-wall regions compared to the core blood flow (Taylor, Figueroa, 2009, Xiao, Humphrey, Figueroa, 2013 and Xiao, Alastruey, Figueroa, 2014). Consequently, computations are limited to the inlet and outlet cross-sections, e.g.

$$A_e = \frac{\rho}{2}\int_{\Gamma_i \cup \Gamma_w} |v|^2(v \cdot n)dx \qquad \text{Equation (1)}$$

Furthermore, we assume the pressure to be nearly constant on the inlet and outlet planes, making $$H(p)=p_i\int_{\Gamma_i}v \cdot ndx + p_o\int_{\Gamma_o}v \cdot ndx + \int_{\Gamma_w}pv \cdot ndx \qquad \text{Equation (2)}$$

When little or no compliance is present, |v·n|<<1 on the wall, the global mass balance compatibility condition yields, $$\int_\Gamma v \cdot ndx = \int_{\Gamma_o} v \cdot ndx + \int_{\Gamma_i} v \cdot ndx = 0 \qquad \text{Equation (3)}$$

letting, $$H(p)=\Delta p\Lambda, \qquad \text{equation (4)}$$

where $\Delta p = p_o - p_i$ is the pressure difference between the outlet and inlet and $\Lambda = \int_{\Gamma_o} v \cdot ndx$ is a term accounting for the flux through surfaces, a term that can be expressed as a function of the inlet surface only by means of Eq. 3.

Regarding the shear energy $S_e$, we consider the contribution over each boundary segment—inlet, outlet and wall—to be effectively zero. On inlet/outlet planes, this term contributes if there are significant gradients in the direction of the boundary normal. While these gradients can occur—particularly in bending or tapering vessels—they are extremely mild and effectively scaled away by the low viscosity of blood. This argument on the flow gradients cannot be assumed near the vessel walls, where a significant wall shear stress is induced. However, as this shear stress is principally orthogonal to the wall velocity (which predominantly dilates in the boundary normal direction), the contribution of these shear stresses to $S_e$ is assumed negligible.

With the assumptions above, the Work-Energy Relative Pressure (WERP) formulation to estimate the pressure difference based on energy contributions yields, $$\Delta p = -\frac{1}{\Lambda}\left(\frac{\partial}{\partial t}K_e + A_e + V_e\right). \qquad \text{Equation (5)}$$

From this equation, we observe that all RHS terms are directly derived from flow data, enabling the computation of the pressure difference. However, we also observe that this computation requires that |Λ|>0 (e.g. that flow is observed through the vascular segment).

2.2. Computation from 4D PC-MRI

Let Vt represent the velocity image acquired at time t, Vt(i, j, k) the velocity field evaluated at time t at the voxel (i, j, k) and Δt the discrete time step between two consecutive acquisitions. We discretize derivatives in Eq. 5 using a central finite difference method and estimate the pressure difference between inlet/outlet planes at time t+½ as $$\Delta p^{t+\frac{1}{2}} = \qquad \text{Equation (6)}$$
$$-\frac{1}{\Lambda(V^{t+\frac{1}{2}})}\left(\frac{K_e(V^{t+1}) - K_e(V^t)}{\Delta t} + A_e(V^{t+\frac{1}{2}}) + V_e(V^{t+\frac{1}{2}})\right),$$

where velocities at t+½ are approximated to second order accuracy $O(\Delta t^2)$ by equation (7)

$$V^{t+1/2} = \frac{1}{2}(V^t + V^{t+1}).$$

Computation of the WERP formulation terms is performed by integrating over a voxelized version of Ω, $I_{ROI}$. Surface integrals are evaluated on the planes obtained by clipping the 3D mask to define inlet $I_{in}^{2D}$ and outlet $I_{out}^{2D}$ cross-sections (see FIG. 3) and the normal vectors $N_2D(i, j)$. The discrete terms are then estimated from the image-based velocity field as, $$\Lambda(V) = dS \sum_{(i,j) \in I_{out}^{2D}} M_{2D}(V)(i, j) \cdot N_{2D}(i, j), \qquad \text{Equation (8)}$$

$$K_e(V) = \rho dV \sum_{(i,j,k) \in I_{ROI}} |M(V)(i, j, k)|^2,$$

$$A_e(V) =$$
$$\frac{\rho}{2} dS \sum_{(i,j) \in I_{in}^{2D} \cup I_{out}^{2D}} |M_{2D}(V)(i, j)|^2 \cdot (M_{2D}(V)(i, j) \cdot N_{2D}(i, j)),$$

$$V_e(V) = \frac{\mu dV}{2} \sum_{(i,j,k) \in I_{ROI}} \mathcal{D}(V)(i, j, k) : \mathcal{D}(V)(i, j, k).$$

where $dS=\Delta x^2$ and $dV=\Delta x^3$ are the pixel surface and voxel volume, respectively, based on the voxel length Δx. The discrete evaluation of all the contributions relies on the definition of the approximated velocity fields M(V) and $M_{2D}(V)$, obtained through averaging over the 3D mask and on the 2D planes defined above, $$M(V)(i, j, k) = \frac{1}{2(1+q)}\sum_{n=o}^{q}(V(i+\delta_{n1}, j+\delta_{n2}, k+\delta_{n3}) + \qquad \text{Equation (9)}$$
$$V(i-\delta_{n1}, j-\delta_{n2}, k-\delta_{n3})),$$

-continued $$M_{2D}(V)(i,j) = \frac{1}{2 \cdot \max(1,q)} \sum_{n=0}^{\max(O,q-1)} (V(i+\delta_{n1}, j+\delta_{n2}) + V(i-\delta_{n1}, j-\delta_{n2})).$$

Figure 4:
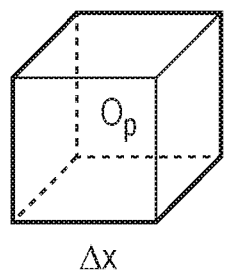
FIG. 4 is a drawing illustrating an aspect of the theoretical basis of the first embodiment of the invention.
Figure 4:
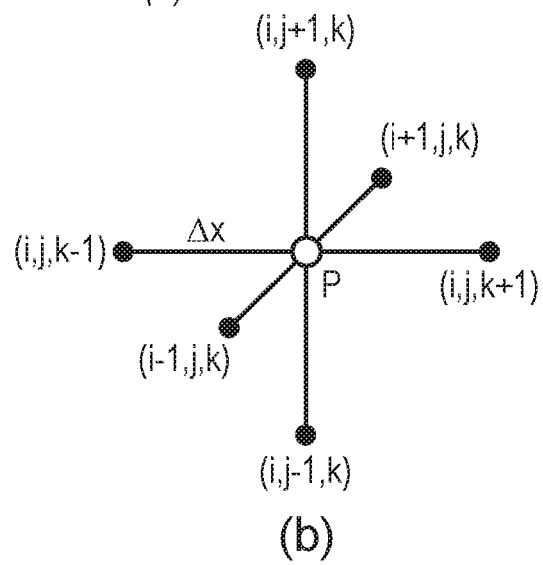
Figure 4:
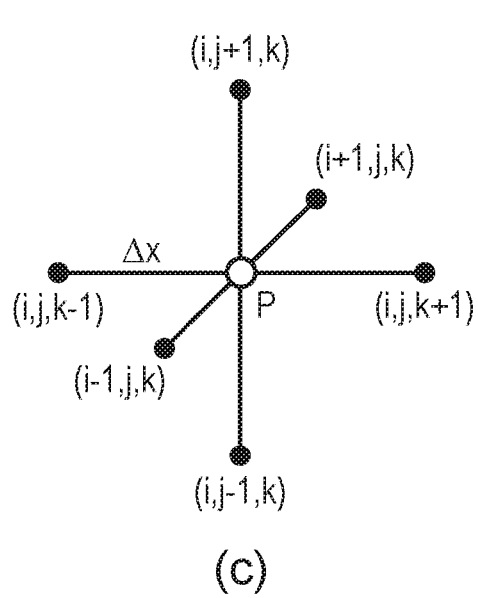
Figure 4:
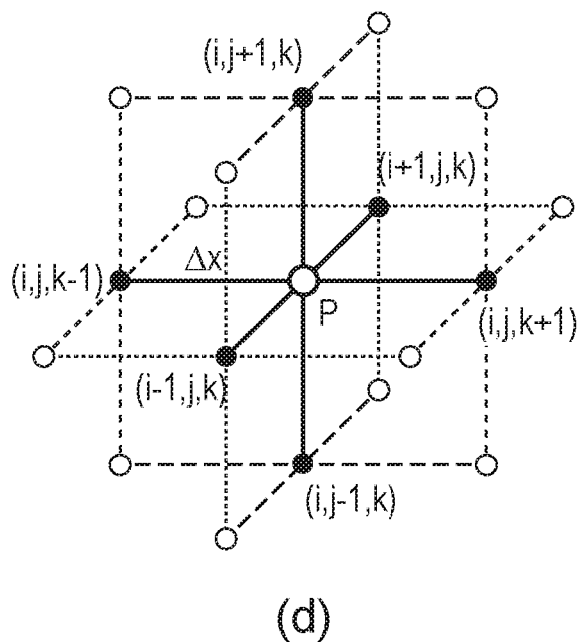

In the above, $\delta_{ij}$ is the Kronecker delta and q is a parameter used to smooth the underlying data based on $O(\Delta x^2)$ approximations to the velocity value (see FIG. 4, which shows a schematic representation of the finite differences central stencils.

Velocity field V evaluation at P=(i,j,k) through operator M(V) using standard (a) and filtered approach (b) and velocity field V derivative evaluation at P=(i,j,k) through operator D(V) using standard (c) and filtered central differences approach (d)).

In the above if q=0, $M(V)(i,j,k)=V(i,j,k)$ and $M_{2D}(V)(i,j)=V(i,j)$ return the velocity measured at the voxel (i, j, k) and (i, j), respectively. Alternatively, if q=3, the measurement of the velocity field is taken as a weighted sum of $O(\Delta x^2)$ approximations based on neighboring voxel measurements, effectively averaging out potential artefacts due to noise.

Similarly, Eq. 8, the discrete tensor D(V) is calculated as, $$D(V)(i,j,k) = (G(V)(i,j,k) + G(V)T(i,j,k)), \quad \text{Equation (10)}$$

where G(V) is a velocity gradient tensor defined as, $$G_{mn}(V)(i,j,k) = \frac{1}{2 \cdot \max(1,q)} \sum_{r=0}^{q} (1-\delta_m)\tilde{D}_n^r V_m(i,j,k), \quad \text{Equation (11)}$$

where $$\tilde{D}_n^r V_m(i,j,k) = \frac{1}{2}(D_n V_m(i+\delta_{r1}, j+\delta_{r2}, k+\delta_{r3}) + \quad \text{equation (12)}$$
$$D_n V_m(i-\delta_{r1}, j-\delta_{r2}, k-\delta_{r3})),$$

and $$D_n V_m(i,j,k) = \frac{V_m(i+\delta_{n1}, j+\delta_{n2}, k+\delta_{n3}) - V_m(i-\delta_{n1}, j-\delta_{n2}, k-\delta_{n3})}{2\Delta x}. \quad \text{Equation (13)}$$

Again, if q=0 velocity gradients are approximated by second order central differences centred at the voxel (i, j, k). Imposing q=3, a filtered approach is adopted, where the velocity derivative is approximated using weighted average of derivatives computed with second order central differences at neighboring voxels, therefore reducing noise contamination (see FIG. 2).

2.3. Required Pre-Processing

Prior to application in a clinical setting, a number of pre-processing steps are required. Field inhomogeneities and eddy currents (Chan, Von Deuster, Giese, Stoeck, Harmer, Aitken, Atkinson, Kozerke, 2014, Moussavi, Untenberger, Uecker, Frahm, 2014 and Rohde, Barnett, Basser, Marenco, Pierpaoli, 2004) are corrected (1) using the pre-processing tools outlined in Bock et al. (2011). Subsequently, a binary mask $I_{ROI}$ is defined (2), based on a thresholding of the velocity magnitude calibrated by the maximum velocity $V_{max}$ (including voxels with a velocity magnitude greater than $S \cdot V_{max}$, with S being the segmentation thresholding parameter). Inlet and outlet points are manually selected by the user (3) depending on the clinical problem under investigation. A skeletonisation of the binary mask is then used to define the inlet and outlet planes perpendicular to the vessel (4). As a result of this process, the binary masks of the raw 3D image and the inlet/outlet planes needed for the WERP computation are defined. Within this work, the image acquisition process was mimicked in silico for the validations tests presented in Results 3.1 and 3.2 and 3.3 in Donati et al *Non-invasive pressure difference estimation from PC-MRI using the work-energy equation* Medical Image Analysis, Vol. 26, pp. 159-172, December 2015. Simulated PC MRI images were subsequently processed following steps (2)-(4) prior to application of the WERP method.

2.4 System Description

Figure 5:
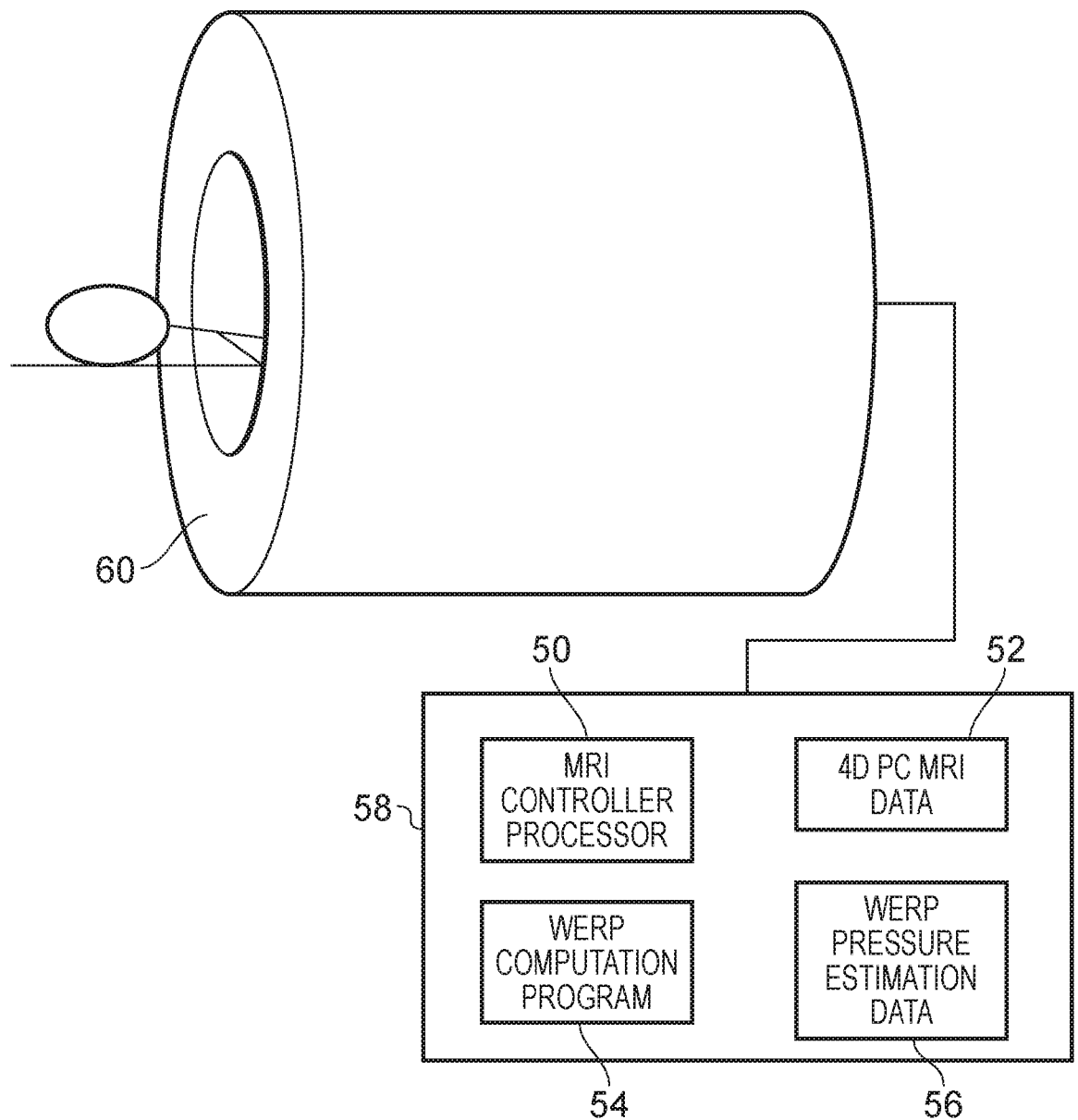
FIG. 5 is a block diagram of a first embodiment of the invention.

FIG. 5 illustrates an example imaging system that is able to apply the above described techniques to calculate blood flow through a blood vessel using the full WERP method. Here, a 4D phase contrast magnetic resonance imaging (4D PC MRI) system 60 is provided, comprising MR imaging coils within which the subject is located, controlled by an MRI imaging control system 58, including an MRI controller processor 50. The MRI imaging control system 58 including the MRI controller processor 50 function in a conventional manner to allow 4 dimensional phase contrast magnetic resonance image data to be obtained, for example of an internal blood vessel of the subject the pressure difference across it is desired to know. For example, it may be desirable to measure transvalvular pressure drops (TPD) along the transvalvular region in the heart, between the left ventricular outflow tract and the vena contracta. Of course, other blood vessels may also be monitored, as desired. For example, it may be possible to take into account secondary branches.

The 4D PC MRI system 58, 60, collects 4D PC MRI data 52 of the imaging subject, which is saved for further processing and analysis. As explained previously with respect to FIG. 1, the complete velocity vector field over the entire imaged plane, and not simply its projection along the insonation line, is available from 4D PC-MRI.

The 4D PC MRI system 58, 60, also includes a WERP computation program 54, which acts to process the 4D PC MRI data 52 as described above in accordance with the WERP processing method described, to obtain WERP pressure estimation data 56. The WERP processing method computes the pressure difference along the vessel as an addition of three rates of energy transfer (kinetic, advective and viscous) divided by the net flow through the vessel, as described above. The resulting WERP pressure estimation data 56 gives an estimate of pressure at each point along the vessel between the measured inlet and outlet planes, taking into effect the vessel walls between the inlet and outlet. It provides a complete solution for every point within the vessel between the inlet and outlet.

Figure 6:
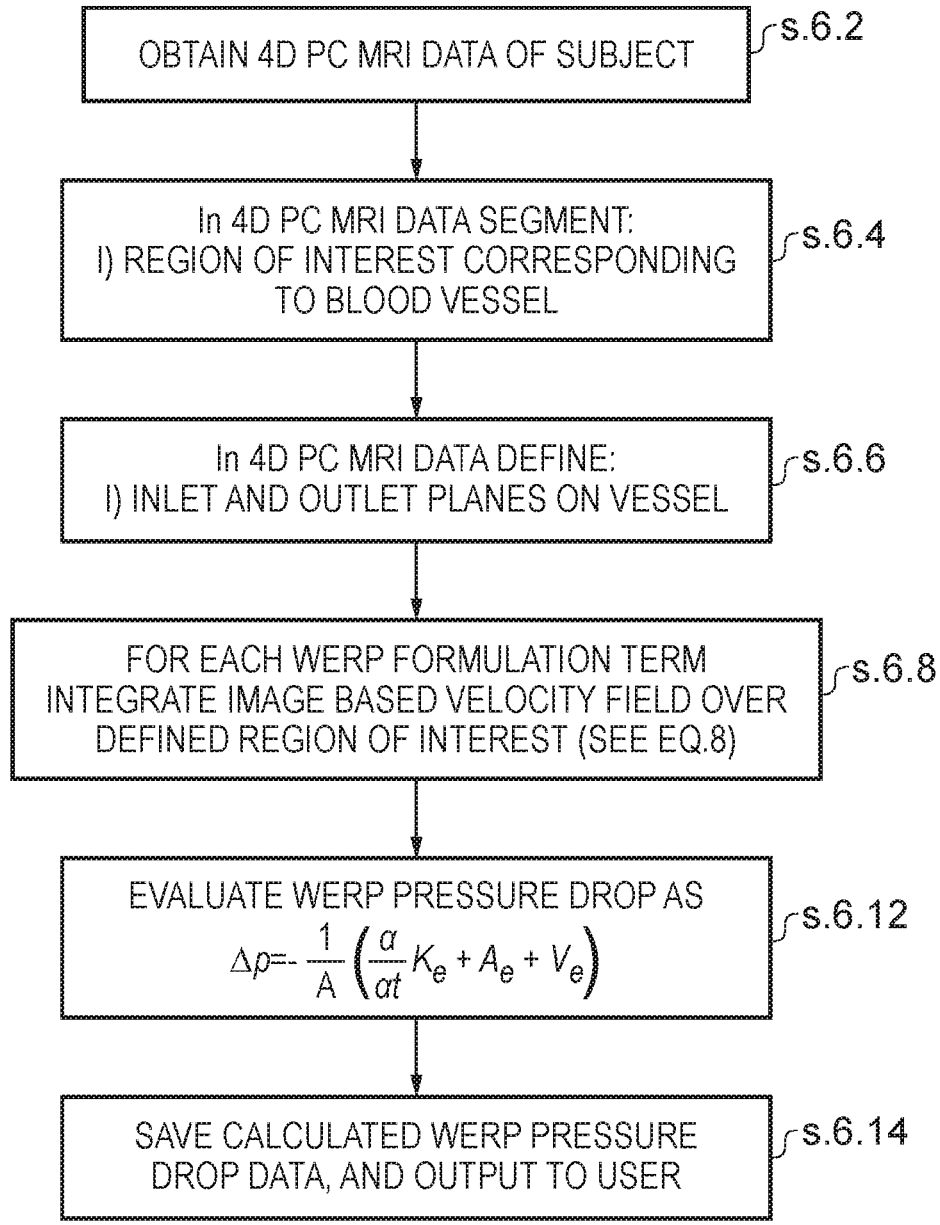
FIG. 6 is a flow diagram relating to the operation of the first embodiment of the invention.

FIG. 6 is a flow diagram summarising some of the important elements of the full WERP process. In step 6.2 the 4D phase contrast MRI data relating to the blood vessel of the subject for which pressure is to be found is obtained. Note that this may be obtained "live" i.e. just before the calculation is performed, or may be recorded or stored data from a previous scan. In this respect, there is no need for the human subject to be present in order for the WERP process to be performed to find the pressure drops, as the process can be run on recorded or stored MRI data.

Figure 3:
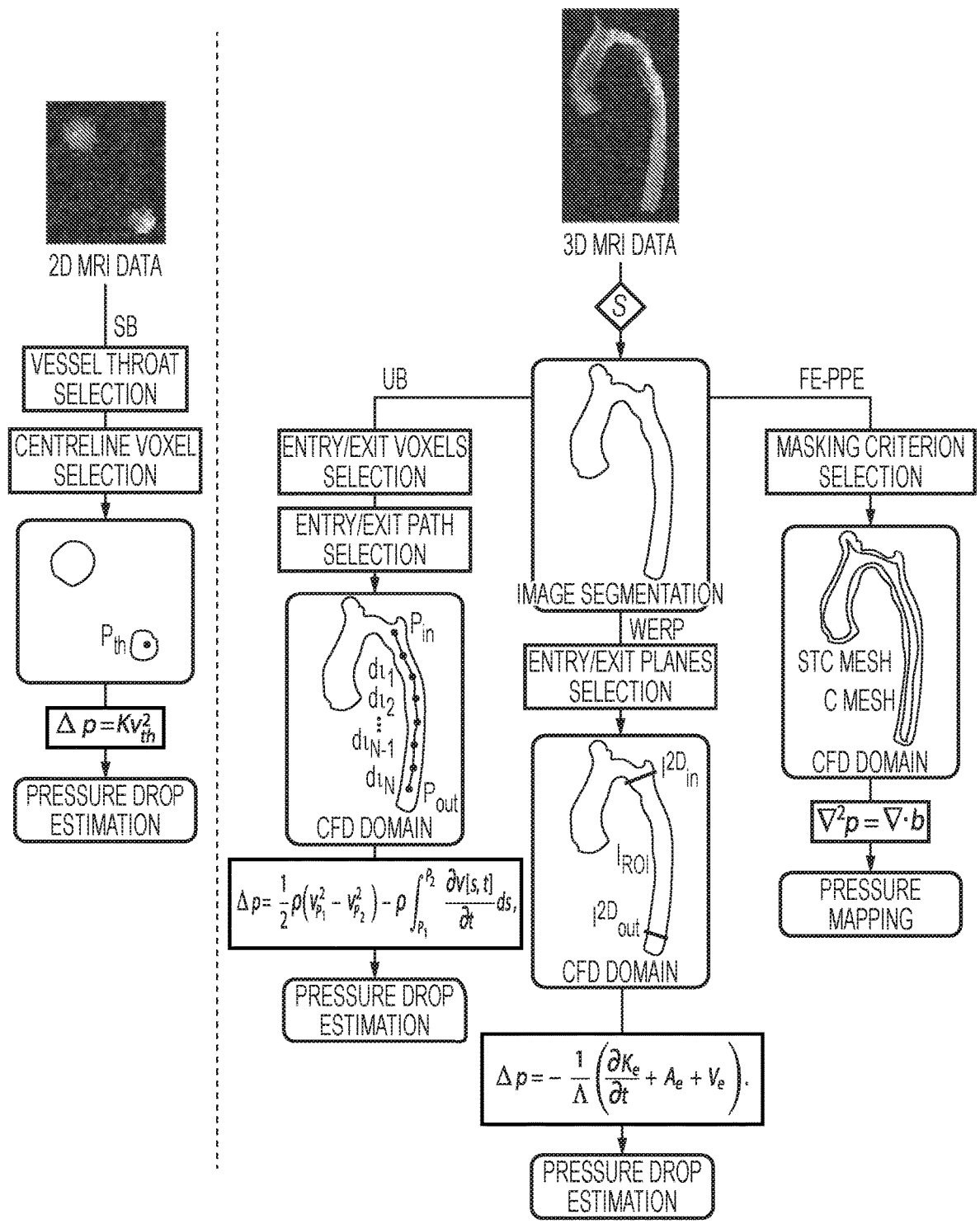
FIG. 3 is a drawing illustrating the comparison of the process of one of the embodiment of the invention with the existing alternatives in the state of the art.

At step 6.4, the 4D PC MRI data is segmented, as shown in FIG. 3, to define the region of interest corresponding to the blood vessel for which the pressure drop is to be found. Then, at step 6.6, and again as shown in FIG. 3, the vessel inlet and outlet planes are defined.

Next, at step 6.8, for each WERP formulation term the image based velocity field from the MRI data is integrated over the defined region of interest. The precise calculations performed are detailed in Equation 8 and the related equations above. The result are a number of individual terms that can then be combined to find the whole pressure drop over the defined region of the vessel, using Equation 5 above, as shown at 6.12. The calculated WERP pressure drop data is then saved, and output to the user, at step 6.14, for example by being displayed on a screen (not shown).

Second and Third Embodiments: Complete Advective WERP and Simplifed Advective WERP The second and third embodiments relate to simplifications of the full WERP process, that mean that less complex imaging modalities which collect less information may be used. In particular, as described below, the complete advective WERP approach may be performed using any modality that renders velocity data in two anatomical planes, for example 2D PC MRI or 3D Doppler ECG, whereas the simplified advective approach may be used with any modality that renders velocity data in a single anatomical plane, for example 2D PC MRI, 3D Doppler ECG or 2D Doppler ECG data. Accessing this partial information (i.e. velocity data in a single anatomical plane) is feasible by Doppler ECG imaging apparatus that are very common in many clinical environments.

There follows a discussion of the approaches, and presentation of various results and comparisons with the Bernoulli based approaches of the prior art.

As shown in the first embodiment of the invention, using the WERP formulation the contributions to the pressure drop due to temporal acceleration (kinetic drops), spatial transport of momentum (advective drops) and friction losses (viscous drops) are revealed to better understand the hemodynamics of the human aorta towards improved stratification of patients[22].

Building on this, we conduct a thorough comparison between drops computed with WERP and Bernoulli formulation on 3D PCMRI (or 4D flow MRI) data, for the assessment of severity of AS on a cohort of 32 patients with BAV. Studying the correlation between non-invasive drop estimates obtained with the different approaches, a consistent overestimation was observed in the Bernoulli formulation. Further investigation demonstrated that this discrepancy is the result of the fact that a Bernoulli approach does not take into account information about the velocity profile. Examining the WERP prediction of the TPD, a clear dependence on the advective drop was observed, particularly in stenosed patients. Utilizing this fact, we propose a novel simplification of the WERP formulation, which improves the accuracy of computed TPD but limits the dependence on comprehensive flow data, enabling estimation from either 2D PCMRI or 3D Doppler echocardiography data. The applicability of the method to 2D Doppler echocardiographic data is also tested.

Material and Methods
Patient Data

For these embodiments, a cohort of 32 subjects with different degree of aortic valve stenosis is selected. Each subject underwent two cardiovascular magnetic resonance scans—one on a 1.5 T system (Avanto, Siemens, Erlangen, Germany) for anatomical imaging, the second on a 3 T system (Trio, Siemens, Erlangen, Germany) for 4D PCMRI assessment, both using a 32-channel cardiac coil. All images were electrocardiogram (ECG)-gated.

Subjects were divided between Group I (n=20) and Group II (n=12) according to an assessment of the mean TPD following current clinical guidelines[23], diagnosing mild stenosis if mean TPD>20 mmHg. The Bernoulli principle using peak velocity values across the valve was used for the computation of these pressure values. Aortic dimensions and hemodynamics data are shown in Table 1.

TABLE 1

Aortic dimensions and flow hemodynamics in n = 32 patients divided in two groups based on the mean systolic pressure drop: Group I ($\Delta p \leq 20$ mmHg, n = 20) and Group II ($\Delta p > 20$ mmHg, n = 12).

|  | Group I | Group II |
| --- | --- | --- |
| Male (%) | 35% | 91% |
| Age | 28.2 ± 14.1 | 38.8 ± 20.2 |
| Aortic Diameters/BSA [mm/m$^2$] | | |
| Left ventricle outflow tract | 13.4 ± 2.6 | 15.4 ± 3.8 |
| Aortic valve | 14.5 ± 1.7 | 17.6 ± 4.0 |
| Brachiocephalic artery | 14.5 ± 1.5 | 20.7 ± 3.9 |
| Left subclavian artery | 12.2 ± 1.2 | 13.8 ± 1.8 |
| Mid descending aorta | 11.1 ± 1.1 | 12.0 ± 1.4 |

Values are mean ± std

Pre-Processing and Definition of Anatomical Regions

4D PC-MRI images field inhomogeneities and eddy currents[24-26] were corrected using the pre-processing tools developed by Bock et al.[27]. The lumen of the left ventricle and aorta were identified using a thresholding criterion based on the peak velocity magnitude, defining a binary mask. A skeletonization algorithm[28] was used to extract the centerline of the aorta and its perpendicular planes.

Pressure drops were computed over three anatomical regions illustrated in FIG. 1A, whereas FIG. 2 illustrates the measurements and the computations required for each approach, whereas FIG. 12A. The assessment of AS was then based on the TPD computed along the TransValvular Region (TVR), between the Left-Ventricular Outflow Tract (LVOT) (Plane 1) and the Vena Contracta (VC) (Plane 2), which are reported in Results, below. The LVOT plane was located 12 mm before the aortic valve plane, following the definition used by Garcia et al.[29], and the VC was detected from the medical image as the plane containing the peak velocity magnitude, which is also the plane of maximum narrowing of the aortic valve jet.

For completeness, pressure drops evaluated in the Ascending Aorta Region (AAR)—from the VC (Plane 2) to the brachiocephalic artery (Plane 3)—and the Descending Aorta Region (DAR)—from the left subclavian artery (Plane 4) to a plane at the same height of the aortic valve plane (Plane 5)—are also included in Supplemental Material B.
Simulated 3D, 2D and Continuous (1D) Doppler Echocardiography In order to remove any observer and inter-modality dependence, echocardiography data was derived by sampling 4D PC-MRI in each subject. Idealized conditions were taken: a perfect alignment between the blood flow jet and the line of insonation, with no shadowing. These conditions enable an optimal comparison between the different mathematical formulations introduced in next section.

Echocardiographic data was simulated in Planes 1 and Plane 2 for the computation of the TPD (see FIG. 2 illustrates the measurements and the computations required for each approach, whereas FIG. 12B, whereas FIG. 2 illustrates the measurements and the computations required for each approach, whereas FIG. 2). Original PC-MRI data was linearly interpolated onto a grid of 1 mm×1 mm sample points in each plane. 3D Doppler echocardiographic acquisitions were defined by projection of the velocity along the direction of insonation, taking into account the funneling effect of the probe. To achieve this, the probe location was simulated 10 cm upstream of the VC in the direction of the aortic jet flow, where the aortic valve jet direction was defined as the direction of the velocity vector at the pixel with maximum velocity magnitude, thus defining an idealized 2D velocity profile by color Doppler. Similarly, a set of 1D velocity profiles from 2D color Doppler acquisition were defined by the intersection of the previously projected velocity field with hypothetical insonation planes—since velocity profiles are non-axisymmetric, a total of 12 profiles containing the peak velocity and with arbitrarily oriented lines (with increments of 15°) were generated in each case (see Supplemental Material D for an illustration of the 2D and 1D profiles in each case). Finally, continuous (1D) Doppler echocardiographic data was simulated using the magnitude of the peak velocity pixel projected in the aortic jet flow direction at each time point.

Non-Invasive Pressure Drop Estimates

To assess the patient-specific severity of AS, we compared TPD obtained using a range of approaches ranging from the most complete (WERP) to the simplest (Bernoulli) formulation. Taking a number of simplifications, the derived approaches can be all obtained from the Navier-Stokes equation for Newtonian isothermal fluids, as extensively reported in Supplemental Material A. For clarification purposes, all the methods compared and the assumptions made to obtain the different formulations are schematically presented in FIG. 2.

The Bernoulli principle is widely accepted in the assessment of AS. Obtained from the Navier-Stokes momentum equation by considering the flow along a streamline, it neglects any contribution from the kinetic and viscous pressure components[30,31]. A series of additional assumptions yields the definition of an approximate pressure drop $\Delta p_{sB}$ in mmHg as, $$\Delta p_{sB} = 4 v_{MAX}^2, \qquad \text{(Equation 101)}$$

where $v_{MAX}$ is the peak velocity at the VC estimated from the 4D PC-MRI image. Factor 4 allows conversion of pressure from Pa to mmHg (133 Pa=1 mmHg), if blood density $\rho=1060$ kg/m$^3$ is assumed. In this work this was referred to as the simplified Bernoulli (sB) formulation[32].

Building on this approach and using the same imaging data, we also accounted for the proximal velocity acquired at the LVOT $V_{PROX}$, thus defining the corrected Bernoulli (cB) pressure drop $\Delta p_{cB} = 4(v_{MAX}^2 - v_{PROX}^2)$[33-35]. Clinical guidelines make use of the corrected formulation in patients evaluation when $v_{PROX} > 1.5$ m/s or $V_{MAX} < 3.0$ m/s. It follows that with Bernoulli-based formulations just one single velocity value or two are needed to estimate the pressure drops. This prompted applicability to continuous 1D Doppler echocardiography, thus enabling definition of pressure drops $\Delta p_{sB}^{D1D}$ and $\Delta p_{cB}^{D1D}$).

The availability of comprehensive velocity fields from 4D PC-MRI also enables computation of the pressure drop using fewer assumptions on the flow. Assuming negligible compliant effects and nearly constant pressure at the inlet and outlet planes of a tubular region, the WERP method[21] approximates the Navier-Stokes equation to compute the pressure drop from 4D PC-MRI data $\Delta p_w$ as, $$\Delta p_W = -\frac{1}{Q}\left(\frac{\partial K}{\partial t} + A + V\right), \qquad \text{(Equation 102)}$$

where Q is the flow rate computed at the outlet, $\partial K/\partial t$ is the temporal derivative of the kinetic energy within the vascular region, A is the advected energy rate describing the energy transfer due to the physical movement of a fluid in and out of the domain, and V is the rate of viscous dissipation describing energy losses due to friction. These quantities were estimated directly from the image as described by Donati et al.[21].

The sum of energy contributions of Equation 102 allows separation of the components, yielding to the definition of the kinetic pressure drop $\Delta p_{Kw} = -1/Q(\partial K/\partial t)$, the advective pressure drop $\Delta p_{Aw} = -A/Q$ and the viscous pressure drop $\Delta p_{Aw} = -V/Q$. As the computation of K and V requires the whole velocity field (volume integrals), contrariwise to A and Q (surface integrals), we looked at approximations eliminating these to reduce the data dependence. This is the reason why the rest of this section focuses on the advective term of the TPD.

The complete advective WERP (cAW) approach estimates the pressure drop $\Delta p_{cAW}$ from the velocity field extracted at the inlet and outlet planes (This is analogous to the previously defined $\Delta p_{AW}$. The notation $\Delta p_{cAW}$ stresses that drops in the complete advective WERP formulation are evaluated using both inlet and outlet planes.). It takes into account the three-dimensionally encoded velocity field over the 2D region instead of the single peak velocity value of sB.

Analogously to the sB approach, the assumption of outlet velocities much larger than inlet velocities triggers the definition of the simplified advective WERP (sAW) pressure drop from the 4D PC-MRI data $\Delta p_{sAW}$, which only accounts for the contribution to the advective energy at the outlet plane.

However, as the availability of 4D PC-MRI velocity fields is limited in clinical practice, the above mentioned WERP-based formulations can also be applied to the more widely used echocardiographic data. Consequently, by using the advective WERP approaches to 3D Doppler echocardiographic images, we estimated drops $\Delta p_{sAW}^{D3D}$ and $\Delta p_{cAW}^{D3D}$ based on the velocity field acquired along the direction of the beam in planes perpendicular to the blood jet at the VC and LVOT.

The sAW approach in particular can be further simplified to compute the advected energy rate A by only relying on velocity values at the VC sampled along a line, therefore yielding the pressure drop $\Delta p_{sAW,1D}^{D2D}$ from 2D color Doppler echocardiographic data.

Within this work we mainly focused on mean pressure drops, as clinically accepted guidelines for the echocardiographic assessment of the AS are based on these. Trivially, the mean pressure drops (or mean pressure drop components) $\overline{\Delta p}$ were estimated as the temporal average of the instantaneous drops during systole $\Delta p(t)$. For completeness, the peak pressure drop (or peak pressure drop component) $\Delta p_{MAX}$ was instead computed as the maximum absolute value of the instantaneous drops.

Results

Analysis of the Pressure Components of the TPD

The impact of the kinetic, advective and viscous pressure components to the TPD was analyzed for both groups of patients by using the WERP formulation. We computed the temporal transient of the drops over systole, together with their peak values (see FIG. 11), with peak values of the kinetic pressure drops evaluated on acceleration and deceleration phases separately. Clear differentiation between groups is revealed for the peak advective (P<0.001) and viscous drops (P<0.001), unlike for the kinetic drops during acceleration (P<0.01).

Subjects in Group II have an average advective TPD (absolute peak of 28.74±6.01 mmHg, accounting for 96.9% of the total TPD on average, range 91.5% to 98.5%) highly dominant over the kinetic term by almost one order of magnitude (absolute peak of 4.76±3.35 mmHg during acceleration and of 4.63±2.96 mmHg during deceleration), and over the viscous term by over two orders of magnitude (absolute peak of 0.14±0.07 mmHg). Prevalence of the advective component is also shown in Group I (accounts for 86.2% of the total TPD on average, range 60.5% to 98.7% although to a lesser extent (absolute peak means of 4.83±3.10 mmHg, 2.51±1.67/0.97±0.08 mmHg and 0.02±0.01 mmHg for the advective, kinetic during acceleration/deceleration and viscous components, respectively).

Comparison of the TPD by WERP and Bernoulli Formulations

We compare the TPD computed from the 4D PC-MRI images with the cAW formulation against results obtained with sAW, sB and cB formulations. We compared the mean pressure drops estimated in the TVR with the different approaches, reporting the linear regression and correlation coefficient on Group I and II, separately. FIG. 12 reveals a consistent overestimation of the drops computed with sB (linear regression slopes 0.492 for Group I and 0.367 for Group II, with average overestimation of 99.1%, range of 49.2% to 145.1%), cB (0.573 for Group I and 0.291 for Group II, with average overestimation of 71.3%, range of 14.6% to 141.1%) and sAW (0.887 for Group I and 0.817 for Group II) formulations. Higher correlations were reported between the cAW approach and each of the compared methods for patients in Group I.

Improved TPD Computation: Understanding the Velocity Field

Finally, we explored the reasons behind the discrepancies highlighted in FIG. 12 between the different methods, at the same time investigating the applicability of the WERP-based formulations to different imaging data. To this end, the advective TPD from the original 4D PC-MRI velocity fields ($\Delta p_{sAW}$) were compared against those computed using simulated and idealized 3D Doppler ($\Delta p_{sAW}^{D3D}$) and 2D Doppler ($\Delta p_{sAW}^{D2D}$) echocardiographic data. Additionally, we reported TPD estimates from the sB approach to simulated continuous Doppler echocardiographic images ($\Delta p_{sB}^{D1D}$).

Figure 13:
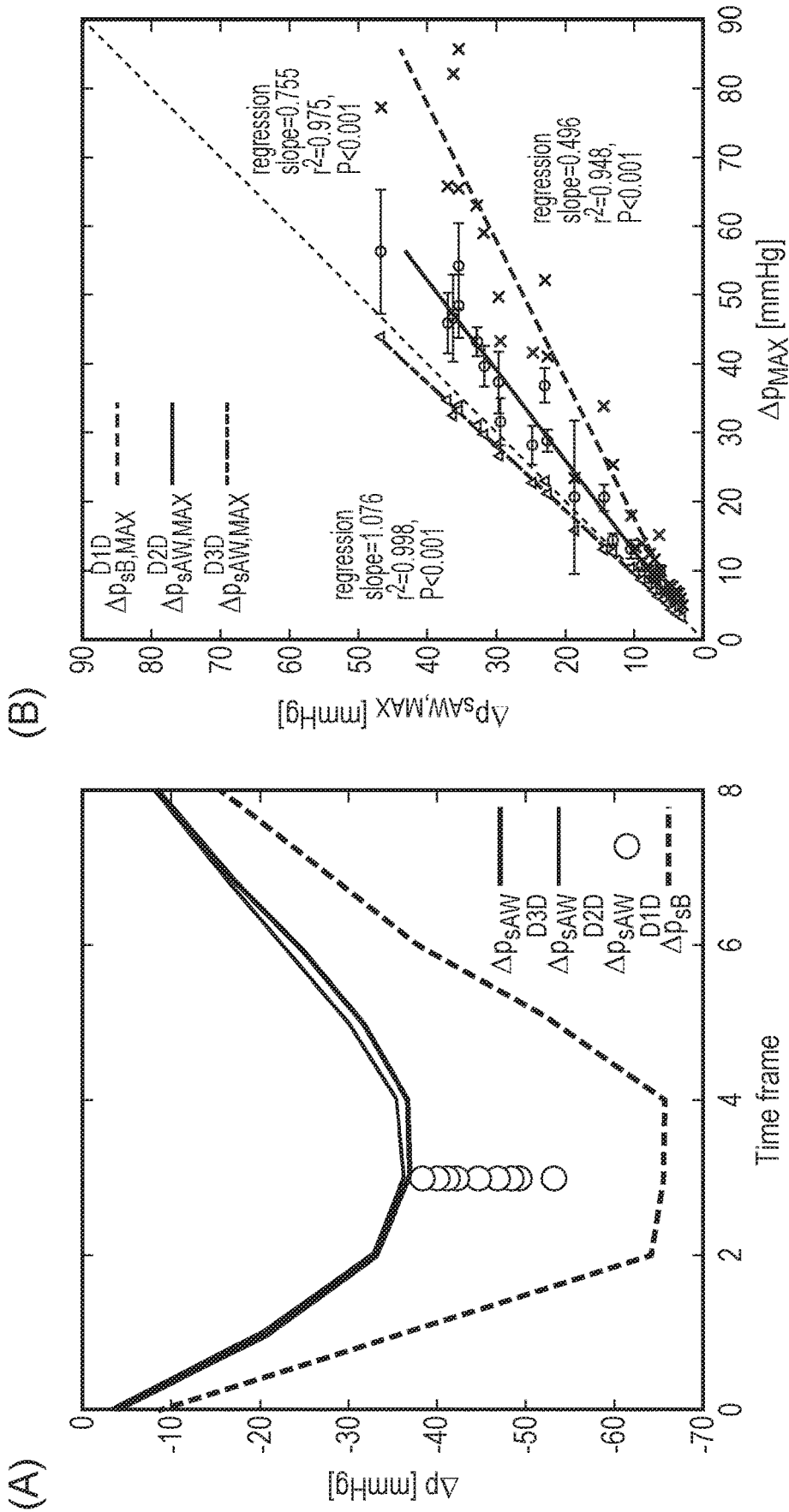

FIG. 13 illustrates the overestimation obtained with the sB formulation (regression slope of 0.496) and with the sAW formulation applied to 1D velocity profiles obtained from an idealized color Doppler acquisition (regression slope of 0.755 when comparing against averaging results from 12 velocity profiles in each case). Variability is introduced by the specific choice of the profile, determined by the insonation plane. A higher correlation is achieved with an idealized color Doppler 3D acquisition using the sAW formulation (regression slope of 1.076).

This section is complemented in Supplemental Material C with an in-silico analysis of three velocity profiles in an idealized stenosis, which demonstrates that the overestimation observed with the Bernoulli formulation is uniquely driven by the shape of the velocity profile.

Discussion

Herein we report the existence of an overestimation of the TPD by the Bernoulli principle, explain its fundamental cause, and propose the formulation to correct it by accounting for the velocity profile in the cross section of the blood jet at the point of the vena contracta.

Figure 11:
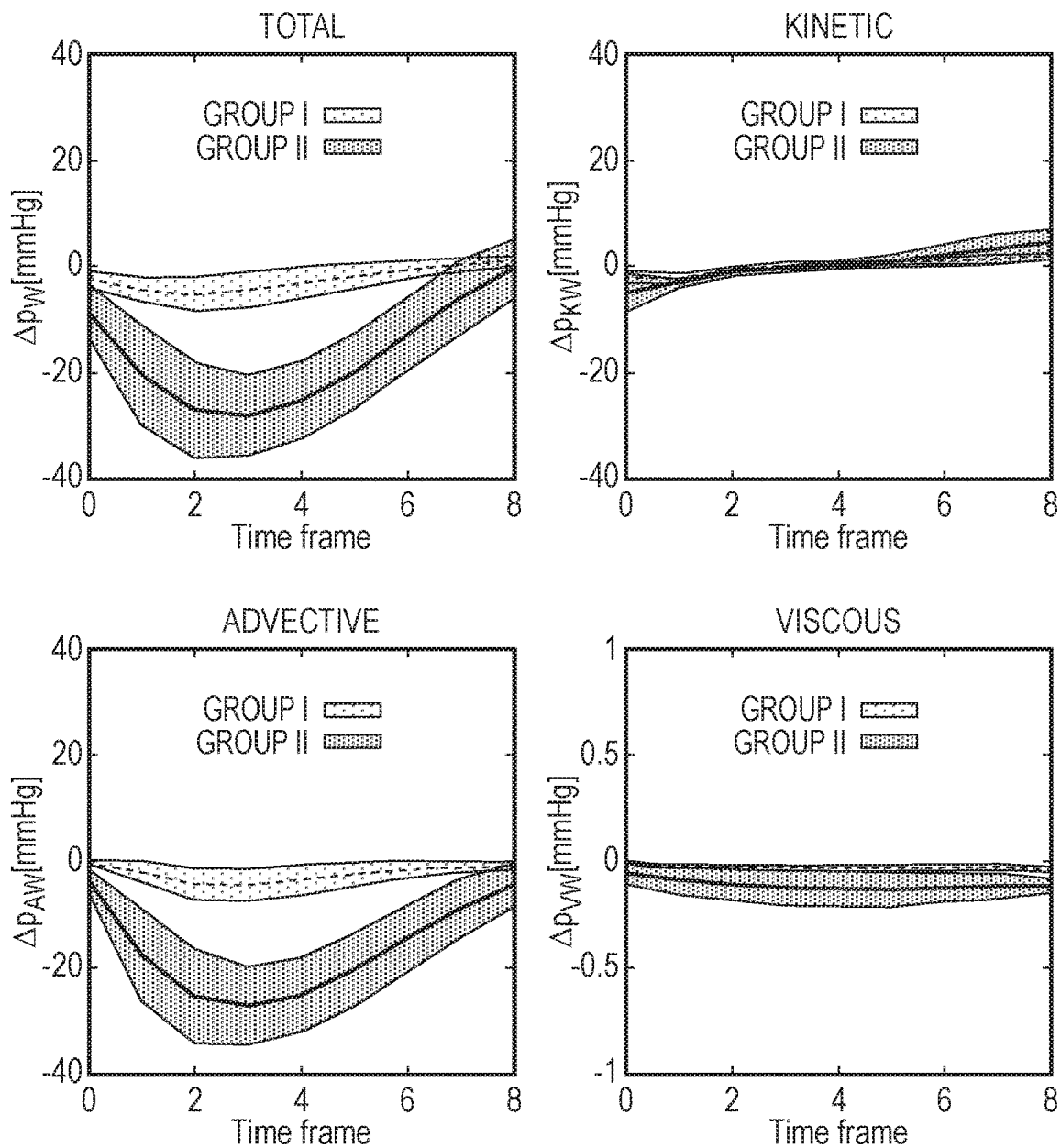
FIGS. 11 to 17(a) and (b) are various graphs illustrating results and effectiveness of embodiments of the invention.

The TPD is driven by the forces that spatially accelerate the flow ejected by the ventricle through a narrow orifice regardless of the other two components of the pressure drops, as illustrated in FIG. 11. Referring to the Navier-Stokes additive terms that contribute to pressure, the transport of momentum (i.e. the advective forces) is the principal contributor to the TPD, with a secondary role played by temporal accelerations (or kinetic drops), and minor impact of viscous dissipative stresses. This finding confirms the sensible choice of the Bernoulli principle to quantify the pressure drop from continuous Doppler recordings adopted in clinical guidelines[23,13,36,37], since the Bernoulli principle is the simplification of the physics of flow through a pipe accounting only to the advective forces.

However, the results described here reveal an overestimation of Bernoulli-based drop computations compared to results obtained with a more complete formulation of the advective drop through the WERP method. The cause of this fundamental bias is that a Bernoulli principle relies on the simplification of the vessel as a single streamline[38-40], as if the vessel was a one-dimensional pipe. But blood flows through 3D vessels, and therefore the computation of the advective energy, and the advective drop, should account for the blood velocity in a cross-section of the vessel, not for only a single peak velocity value. Only if blood velocity profiles were flat, with all particles of the cross section of a vessel having the same velocity, the Bernoulli principle could be adopted without any loss of accuracy (see Supplemental Material C below for a quantitative description of the error in three idealized velocity profiles).

Figure 17A:
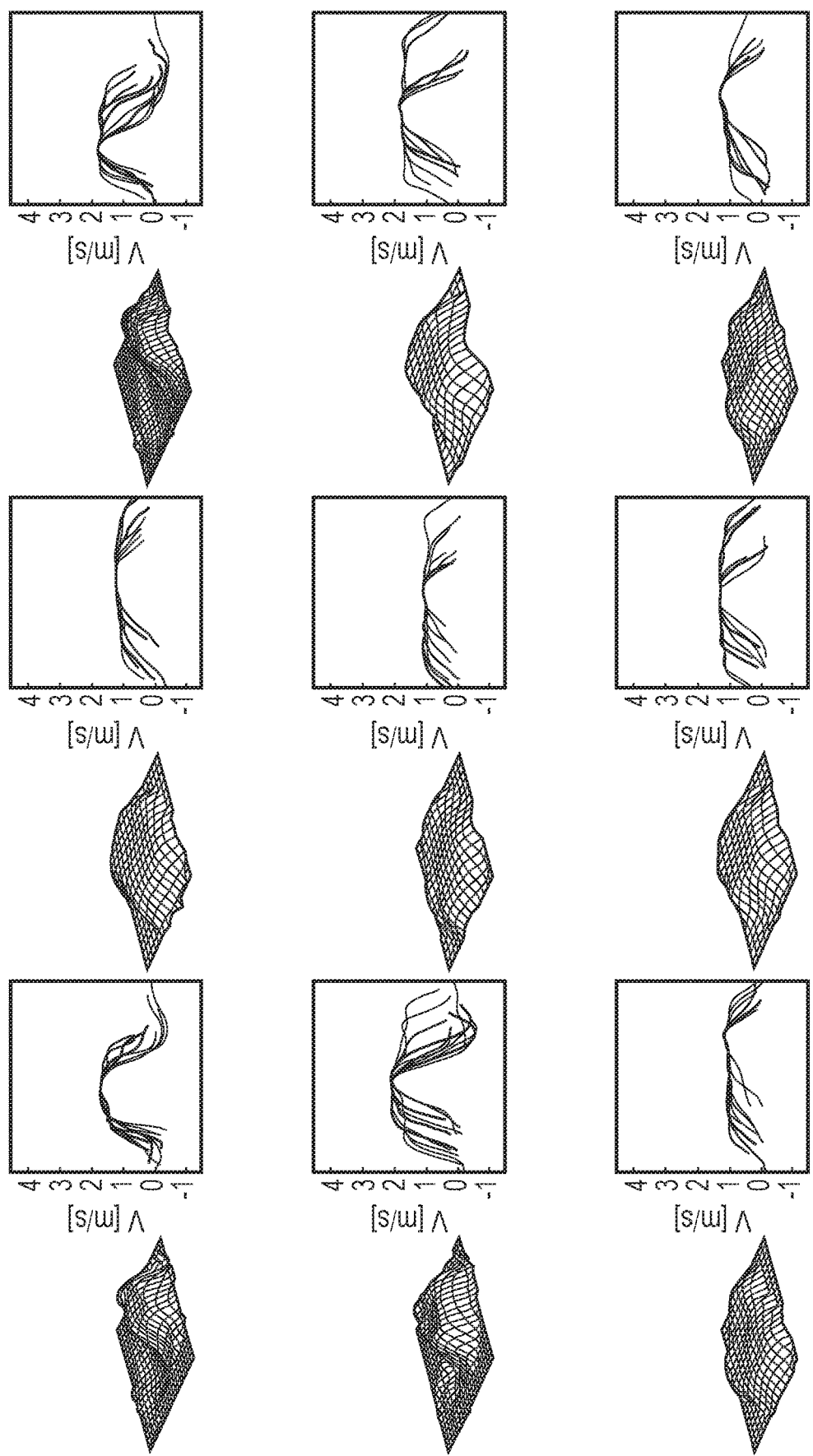
Figure 17A:
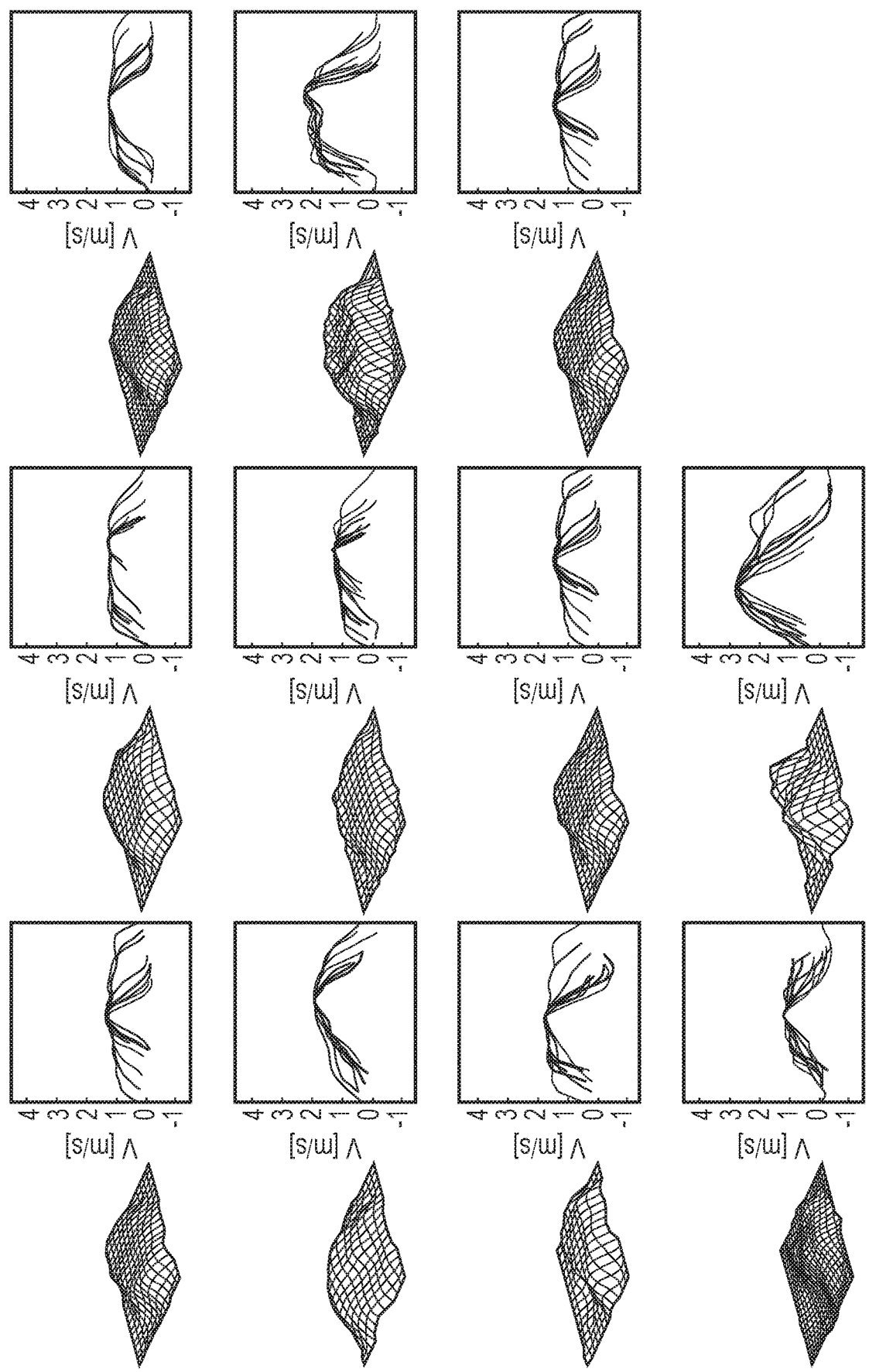

The analysis of our cohort of 32 subjects reveals a large variability in the morphology of the velocity profiles, as illustrated in FIG. 17. As a consequence, the amount of overestimation of the Bernoulli principle is heterogeneous: in the group of stenosed cases Bernoulli overestimated the TPD of 99.1% on average (range of 49.2% to 145.1%) with the simplified and of 71.3% (range of 14.6% to 141.1%) with the corrected formulation, leading to a poor linear regression fitting (see FIG. 12, panels A & B). As an additional reference, in-silico results of Supplemental Material C reveal how the shape of a perfect paraboloid with β=2 introduces an overestimation of 100.9%. The magnitude of proposed correction is therefore quite large and variable, and justifies therefore the need for further research to quantify its impact in the stratification of subjects with valve stenosis.

Our mathematical analysis reveals that, as in the widely adopted Bernoulli formulations, the adoption of sensible assumptions simplify the computation of the advective TPD to only account for the velocity at the inlet and outlet of the vascular domain. This finding is quite relevant for the clinical translation of our findings, since velocity data is only needed at two planes of the vascular anatomy, and not in the entire lumen or ventricular blood pool. Even more, the need for data in the proximal (inlet) region is acknowledged in guidelines only for cases with small level of stenosis, where the corrected Bernoulli formulation should be used[23,34]. Our results confirm the improved accuracy of this strategy for the control cases, but illustrate an increment in the discrepancy with the adoption of a corrected Bernoulli formulation in the mild-to-severe disease cases (drop of correlation and slope in Group II against Group I with correction, compare panels A and B in FIG. 12). These findings suggest that, as currently done in most practical clinical situations, accounting only for the outlet velocity profile (at the point of the vena contracta), neglecting the proximal velocities, is a sensible methodological strategy. The goal of a non-invasive method to stratify VS is then set in the robust and accurate assessment of the advective energy at the point of the vena contracta.

Our results then reveal how this computation of the advective drop depends on the amount, and quality, of data available about the velocity at the point of the VC. We provide the mathematical formulation adapted to different sources of blood velocity data, and analyze the existence of fundamental biases between them. Our results reveal that idealized 3D echocardiographic data, offering a 2D velocity profile at the VC with artifacts from the funneling effect and from the projection of the velocity alongside the line of insonation, introduce a small bias (slope of the regression line of 1.076, see FIG. 13). Accounting for the same artifacts, but with only the information of a part of the 2D velocity profile along one line of insonation as with a 2D echo probe, advective energy is overestimated (slope of the linear regression of 0.755, see FIG. 13). And if only a peak value is available, and the formulation then reduces to the Bernoulli equation, the overestimation is the largest (slope of 0.496, see FIG. 13). The translation of the theoretical finding is thus feasible to a wide range of imaging acquisition protocols and modalities, and further research is needed to define the optimal strategy to control the location of the vena contracta to be imaged (point of maximum advective drop), to identify the direction of the jet and its perpendicular plane, and to maximize the amount and quality of velocity data at that plane.

Our findings also offer a plausible explanation for the overestimation of the TPD using continuous Doppler echocardiography compared to catheter recordings, currently attributed to the pressure recovery after the narrowing of the jet across the valve[5,6,9]. The fundamental cause is the intrinsic assumption of the Bernoulli principle of the reduction of the vessel flow to a single streamline. This work demonstrates that, accounting for the physical principles that govern human hemodynamics (the Navier-Stokes momentum equation) in order to compute the pressure drop that best explains the changes observed in a dense velocity field, the simplifications made by the Bernoulli equation introduce an overestimation of the TPD.

Supplemental Material

A. Mathematical Details Behind the WERP Pressure Drops Estimates

The original form of the WERP formulation is defined from the Navier-Stokes equation based on the work-energy principle—as presented by Donati et al.—and estimates the pressure drop $\Delta p_w$ across the vascular region $\Omega$ with inlet plane $\Gamma_{INLET}$ and outlet plane $\Gamma_{OUTLET}$ defined from the lumen segmented from the 4D PCMRI image as, $$\Delta p_W = -\frac{1}{Q}\left(\frac{\partial K}{\partial t} + A + V\right). \quad \text{(Equation A.1)}$$

The blood flow rate Q, the kinetic energy K, the advective energy rate A and the viscous dissipation rate V can be evaluated by solving numerical surface and volume integrals as, $$Q = \int_{\Gamma_{OUTLET}} v \cdot n dx = -\int_{\Gamma_{INLET}} v \cdot n dx, \quad \text{(Equation A.2)}$$

$$K = \frac{\rho}{2}\int_\Omega (v \cdot v) dx,$$

$$A = \frac{\rho}{2}\left(\int_{\Gamma_{INLET}} |v|^2 (v \cdot n) dx + \int_{\Gamma_{OUTLET}} |v|^2 (v \cdot n) dx\right),$$

$$V = \frac{\mu}{2}\int_\Omega D(v):D(v) dx,$$

where v is the three-dimensional time-dependent velocity field at the generic voxel, n is the normal direction on the inlet/outlet plane, $\rho=1060$ kg/m$^3$ and $\mu=0.004$ Pa·s are the blood density and dynamic viscosity, respectively, and $D(\bullet)=[\nabla(\bullet)+\nabla(\bullet)^T]$. Using separation of the pressure components the complete advective pressure drop evaluated using the WERP method $\Delta p_{cAW}=-A/Q$ yields from Equation A.2, $$\Delta p_{cAW} = \quad \text{(Equation A.3)}$$
$$-\frac{\rho}{2}\left(\int_{\Gamma_{OUTLET}} |v|^2(v \cdot n)dx + \int_{\Gamma_{OUTLET}} |v|^2(v \cdot n)dx\right) \Big/ \int_{\Gamma_{OUTLET}} v \cdot n dx,$$

therefore reducing the drops computation to surface integrals on the inlet and outlet planes and making it applicable to 2D PCMRI or 3D Doppler echocardiographic data.

Equation A.3 can be further simplified by assuming outlet velocities much larger than inlet velocities (which is likely to hold in the transvalvular region defined from the LVOT to the VC, especially in stenosed cases) as, $$\Delta p_{sAW} = -\frac{\rho}{2}\int_{\Gamma_{OUTLET}} |v|^2(v \cdot n)dx \Big/ \int_{\Gamma_{OUTLET}} v \cdot n dx. \quad \text{(Equation A.4)}$$

The sAW approach can be further reduced to estimate the advective energy rate from velocity values along of the VC along a single line, not in the complete perpendicular plane, thus enabling applicability to 2D color Doppler echocardiographic images. Equation A.4, by replacing the surface integrals at the outlet plane for line integrals along the line $\lambda$ defined by intersecting the hypothetical insonation plane with the outlet plane of the aortic lumen plane, and by considering the fact that velocity values are already projected in the direction of the line of insonation, can be rearranged as, $$\Delta p_{sAW} = -\frac{\rho}{2}\int_\lambda |v|^3 d\lambda \Big/ \int_\lambda |v| d\lambda \quad \text{(Equation A.5)}$$

This enables the use of the WERP formulation to compute advective drops based on 2D color Doppler echocardiography.

It is worth noting that advective WERP and Bernoulli formulations are similar—as they both characterize the pressure drop using advective effects—and the mathematical link between them is here explained. In the WERP approach, the blood flow rate Q can be indifferently estimated at the inlet or outlet planes defined from the image data as, $$Q = \int_\Gamma v \cdot n \, dx = v_{MAX} \Psi \quad \text{(Equation A.6)}$$

Here, $v_{MAX}$ is the maximum velocity at the inlet/outlet plane and $\Psi = \int_\Gamma \Phi \, dx$, where $\Phi$ is the normalized shape function in the normal direction for the inlet/outlet velocity profile. Using the cAW formulation in Equation A.3 leads to, $$-\Delta p_{cAW} Q + \frac{\rho}{2} \int_{\Gamma_{INLET}} v_{MAX,INLET}^3 \, dx + \int_{\Gamma_{OUTLET}} v_{MAX,OUTLET}^3 \, dx = 0. \quad \text{(Equation A.7)}$$

If we assume velocity at the planes mainly aligned to the planes normal n, substitution of Equation A.6 (selectively evaluated at the inlet/outlet planes) into Equation A.7 yields, $$\Delta p_{cAW} = \frac{\rho}{2}(v_{MAX,OUTLET}^2 Z_{OUTLET} - v_{MAX,INLET}^2 Z_{INLET}), \quad \text{(Equation A.8)}$$

where $Z_{INLET} = \int_{\Gamma_{INLET}} \Phi_{INLET}^3 \, dx / \Psi_{INLET}$ and $Z_{OUTLET} = \int_{\Gamma_{OUTLET}} \Phi_{OUTLET}^3 \, dx / \Psi_{OUTLET}$ are functions depending on the normalized profile shape only. Consequently, in the hypothesis of a flat velocity profile (i.e. $v_{OUTLET} = v_{MAX,OUTLET}$ and $v_{INLET} = v_{MAX,INLET}$ as in Bernoulli based formulations) and with blood density $\rho = 1060$ kg/m³, Equation A.8 simplifies to the cB formulation $\Delta p_{cB} = 4(v_{OUTLET}^2 - v_{INLET}^2)$. From Equation A.7, in the hypothesis of $v_{OUTLET} \gg v_{INLET}$ the sAW formulation in Equation A.4 can be expressed as, $$\Delta p_{sAW} = \frac{\rho}{2} v_{MAX,OUTLET}^2 Z_{OUTLET}, \quad \text{(Equation A.9)}$$

that assuming a flat velocity profile yields again the sB formulation $\Delta p_{sB} = 4 v_{OUTLET}^2$.

B. Aortic Pressure Drops Downstream of the Aortic Valve

Figure 14:
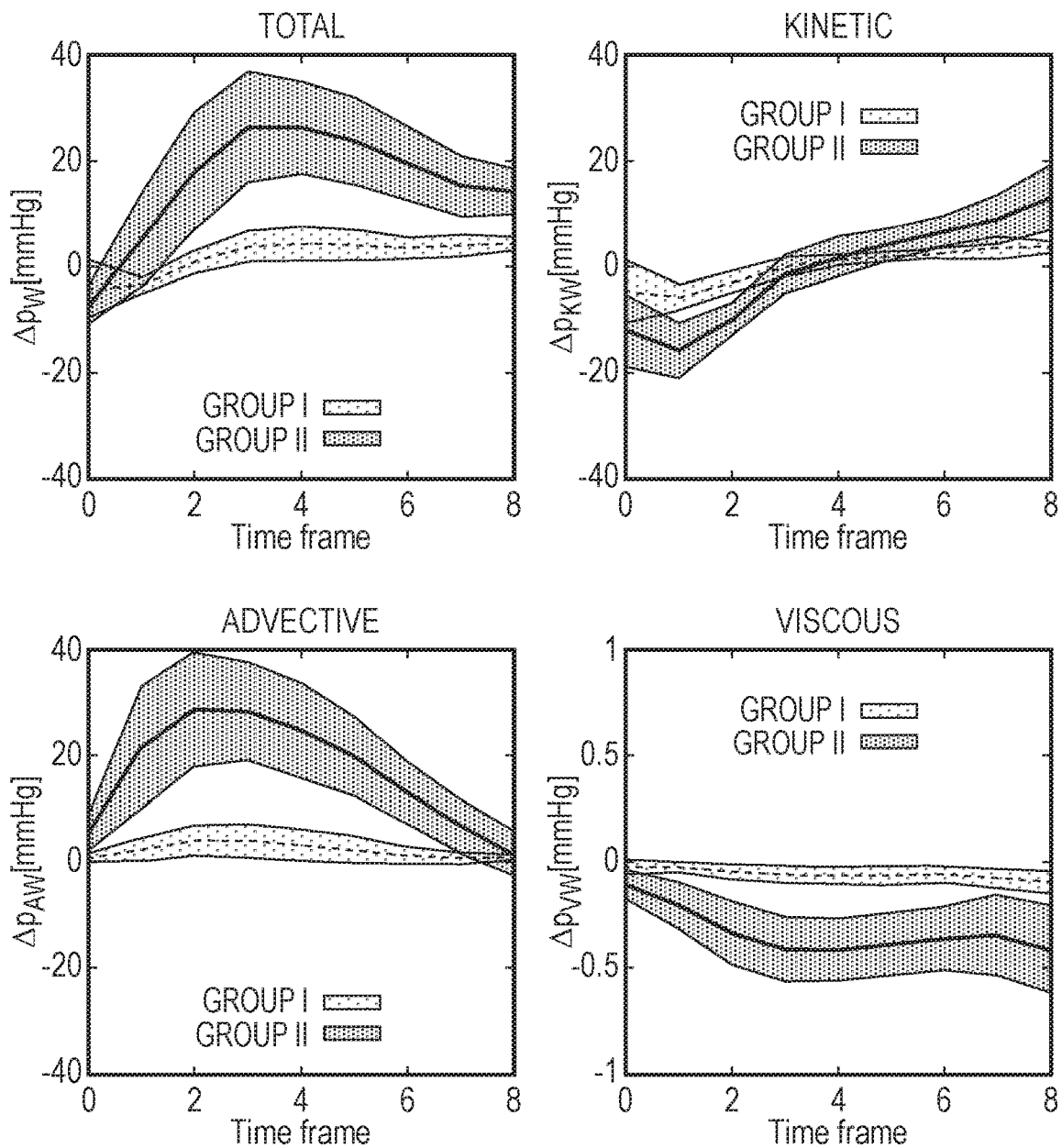
Figure 15:
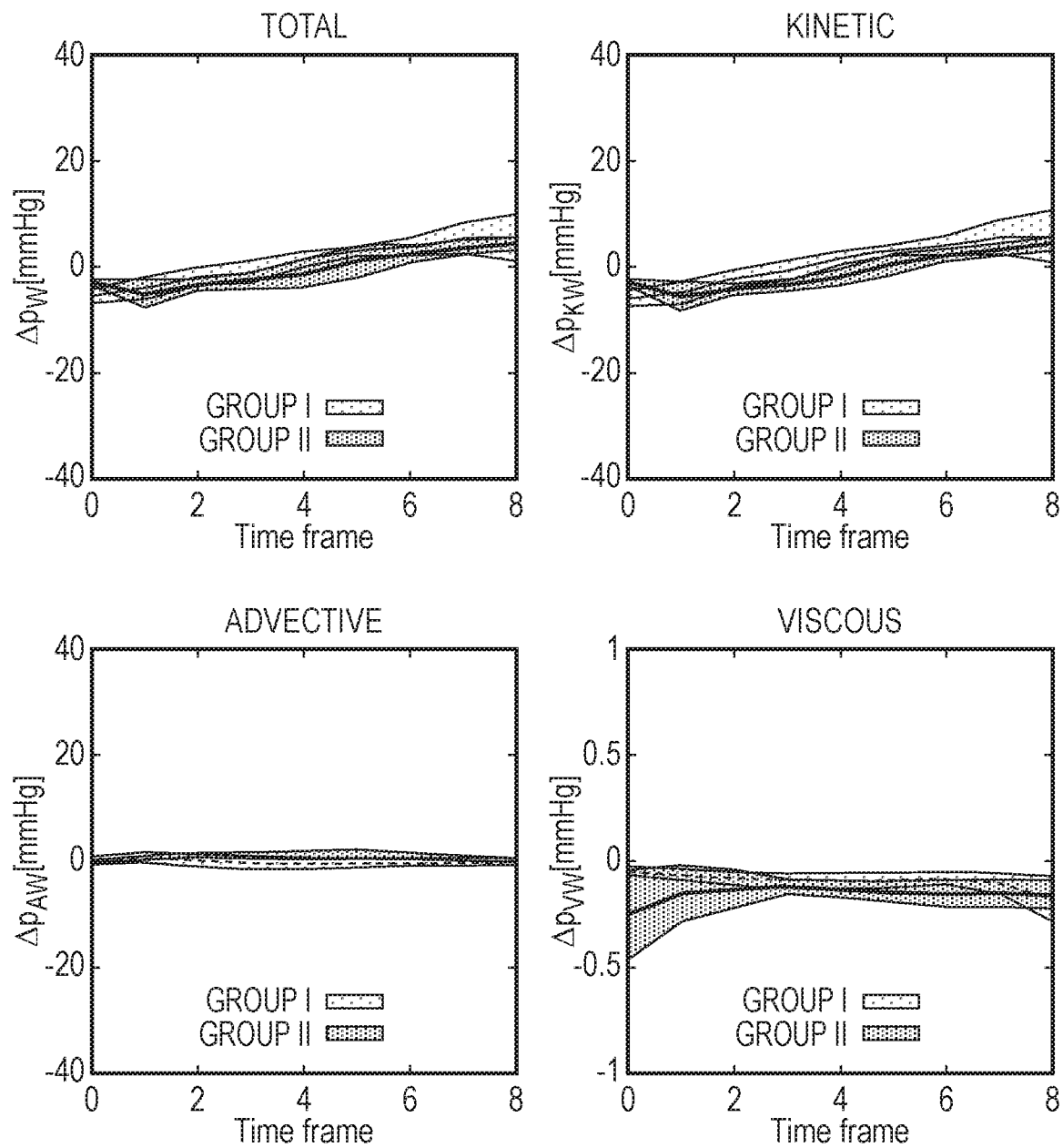

FIG. 14 and FIG. 15 show the temporal transients of the averaged pressure drop components (total, kinetic, advective and viscous) during systole for the two groups of patients respectively obtained in the AAR and DAR defined above. Tabulated results report how the widening of the aortic flow jet downstream of the VC captured in the AAR causes a recovery of the total TPD in Group II subjects, with drop magnitudes comparable with that observed in the TVR (see FIG. 11) but with opposite sign (absolute peak means of 28.74 mmHg in AAR and 31.84 mmHg in TVR). Once again, in Group II the spatial acceleration effects due to aortic morphological changes are dominant over dissipative losses by approximately two orders of magnitude (absolute peaks mean of (0.51 mmHg), with an increased impact of the kinetic term to the total pressure drop (absolute peaks mean of 16.30 mmHg during acceleration and 14.14 mmHg during deceleration). Clear differentiation is shown between patients in Group I and II for all the pressure terms.

In the DAR, the total pressure drops decrease in both groups, with the kinetic component prevalent over others and the advective component sensibly reduced, due to the absence of abrupt variations in the aortic geometry or obstacles in the blood flow hemodynamics. These values are similar to previously reported results in healthy controls[22].

C. The Impact of the Velocity Profile on the Pressure Drop Estimation

The observed difference between WERP and Bernoulli formulations is experimentally verified with a in silico study. A steady flow on a straight tube with a change of diameter is considered. Inlet and outlet velocity fields v(x,y) were imposed analytically using the generic formula for poweroids, $$v(x, y) = v_{MAX}\left(1 - \frac{((x - x_C)^2 + (y - y_C)^2)^{\beta/2}}{R^\beta}\right), \quad \text{(Equation III.1)}$$

where $v_{MAX}$ is the peak velocity, $x_c$ and $y_c$ are the coordinates of the center, R is the radius and $\beta$ is a coefficient accounting for the shape of the profile. We defined a reference case, by choosing the pipe dimensions and flow properties such as the cardiac output CO=5 L/min, the ratio between outlet and inlet radii $R_{OUTLET}/R_{INLET} = 0.25$, the density $\rho = 1060$ kg/m³ and viscosity $\mu = 0.004$ Pa·s to be representative of those in the human thoracic aorta in the presence of AS. Additionally, we selected a spatial discretization dx=0.5 mm and a velocity shape coefficient $\beta = 4$ to reproduce a quasi-paraboloidal profile. We thus compared the pressure gradient ratio $PGR = \Delta p_{cB}/\Delta p_{cAW}$ estimated with cB and cAW formulations, selectively testing: (1) the impact of the cardiac output (CO=4 L/min and CO=6 L/min), (2) the stenosis level in terms of the ratio between radii ($R_{OUTLET}/R_{INLET} = 0.125$ and $R_{OUTLET}/R_{INLET} = 0.5$), (3) the spatial discretization (dx=0.25 mm and dx=1 mm) and the (4) shape of the velocity profile in terms of the shape coefficient ($\beta = 2$ and $\beta = 10$), in order to reproduce configurations that are likely to be found in the human aorta, spanning from paraboloidal ($\beta = 2$) to blunt profiles ($\beta = 10$), see FIG. 8.

Results show a global overestimation obtained with the Bernoulli approach, independent of the spatial discretization, the outlet/inlet radii ratio or imposed flow rate. On the contrary, the difference between WERP and Bernoulli estimates is highly dependent on the shape of the 3D velocity profile, with minimal gap obtained with blunt profiles (ratio of PGR=1.18).

D. Velocity Profiles at the Vena Contracta from PCMRI Data

Simulated 3D color Doppler echocardiography velocity profiles from PCMRI data at the VC are shown in FIG. 17, with surface plots of the 2D velocity field and 12 curves for each case showing the 1D velocity profile obtained as explained previously. Velocity profiles are generally blunt, with $v_{MAX} < 2.5$ m/s for subjects in Group I, clearly showing lower variability of the velocity profiles when compared to subjects in Group II, where peak velocities are $v_{MAX} \geq 2.5$ m/s. The velocity profile is highly non-axisymmetric for Group II patients, therefore motivating the larger variability obtained in this group.

2nd Embodiment: System Description

Figure 9:
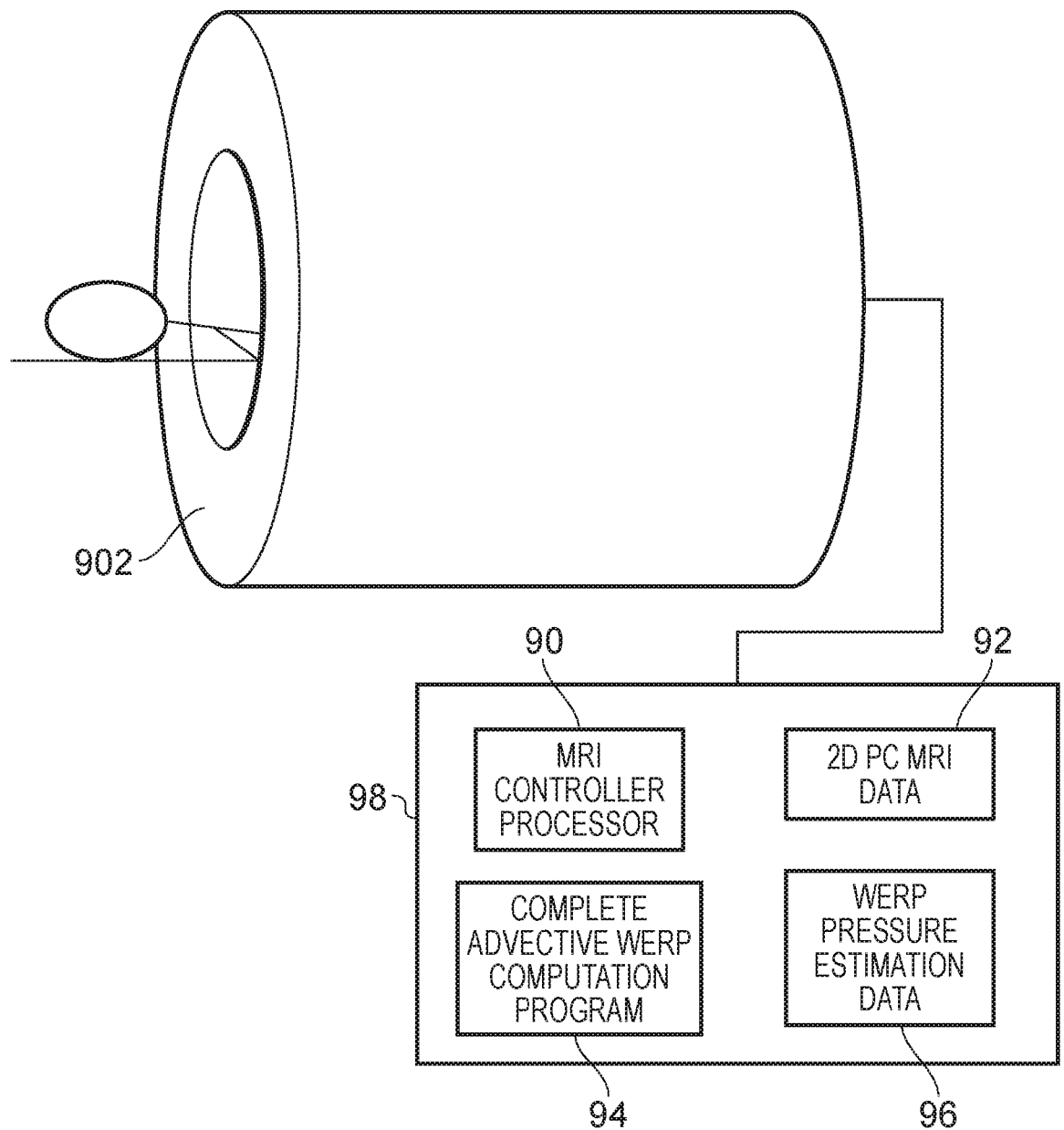
FIG. 9 is a block diagram of a second embodiment of the invention.

The second embodiment relates to performing only a subset of the WERP processing, by considering only the advective term of the full WERP equation. As such, less information is required, and simpler imaging systems may be used, particularly 2D PC MRI systems, and 3D Doppler ECG systems. FIG. 9 is a block diagram of a 2D MRI system that may be used to perform the processing to calculate the pressure drop.

Here, a 2D phase contrast magnetic resonance imaging (2D PC MRI) system 902 is provided, comprising MR imaging coils within which the subject is located, controlled by an MRI imaging control system 98, including an MRI controller processor 90. The MRI imaging control system 98 including the MRI controller processor 90 function in a conventional manner to allow 3 dimensional phase contrast magnetic resonance image data to be obtained, for example of an internal blood vessel of the subject the pressure difference across it is desired to know. For example, it may be desirable to measure transvalvular pressure drops (TPD) along the transvalvular region in the heart, between the left ventricular outflow tract and the vena contracta. Of course, other blood vessels may also be monitored, as desired.

The 2D PC MRI system 98, 902, collects 2D PC MRI data 92 of the imaging subject, which is saved for further processing and analysis.

The 2D PC MRI system 98, 902, also includes a complete advective WERP computation program 94, which acts to process the 2D PC MRI data 92 as described above in accordance with the complete advective WERP processing method described, to obtain WERP pressure estimation data 96. The complete advective WERP processing method is a simplification of the WERP equation by only taking one of the three additive terms of energy, the advective term. The resulting pressure estimation data 96 gives an estimate of pressure at the measured inlet and outlet planes, but neglects the effects of the vessel walls between the inlet and outlet. As such, it does not provide a complete solution for every point within the vessel between the inlet and outlet, but instead provides solutions for the inlet and outlet only, but from which pressure drop across the vessel can then be found.

Figure 10:
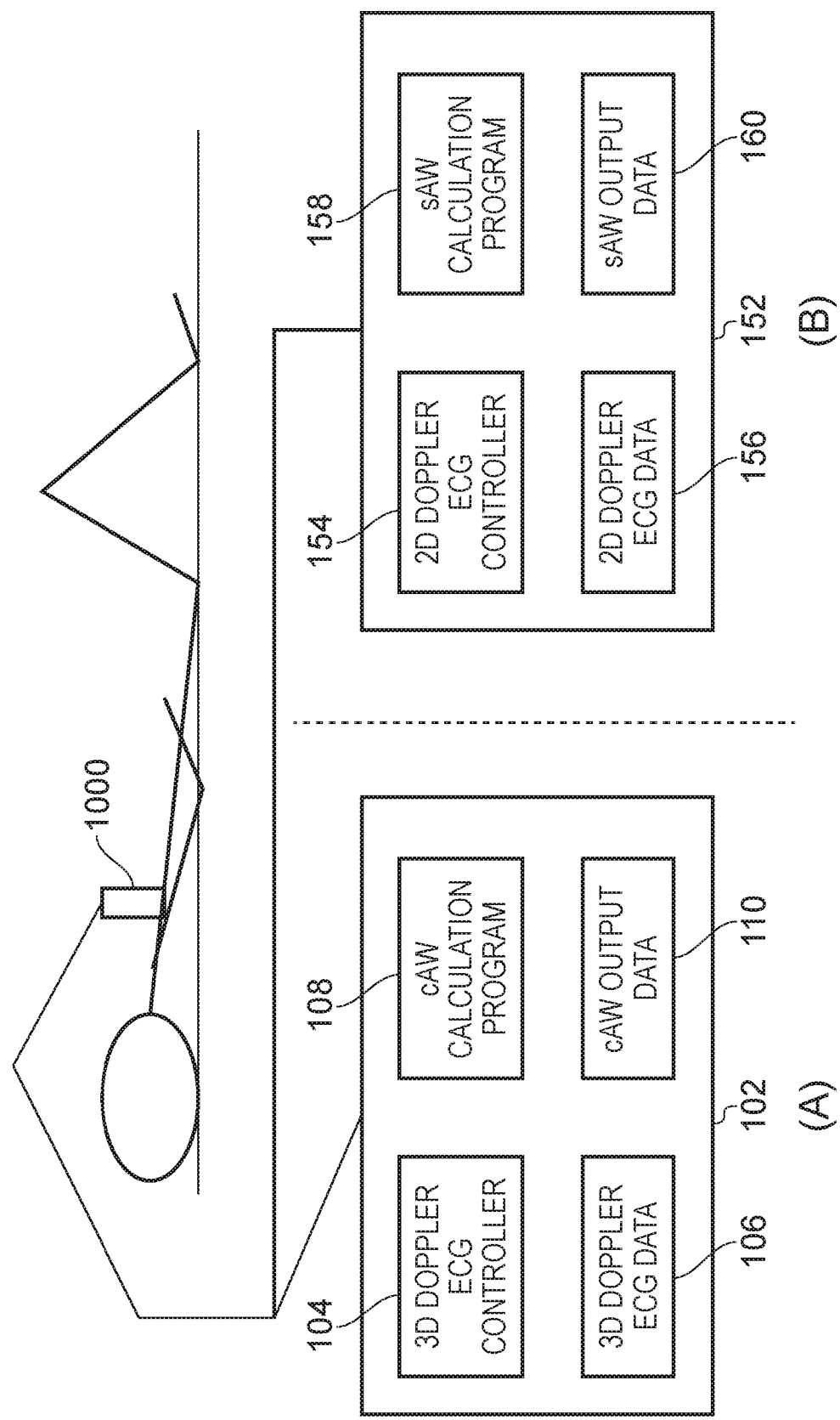
FIG. 10 is a block diagram of a second and third embodiment of the invention.

FIG. 10(A) illustrates the 3D Doppler ultrasound ECG equivalent system. Here a transducer 1000 obtained 3D Doppler measurements from the subject, under the control of 3D Doppler ECG system 102, comprising 3D Doppler ECG controller 104. The system produces 3D Doppler ECG data 106, and which is then used as an input to the cAW calculation program 108, which performs the necessary processing as described previously to find solutions for the inlet and outlet planes of the vessel being monitored, which is then stored and output as cAW output data 110.

Figure 7:
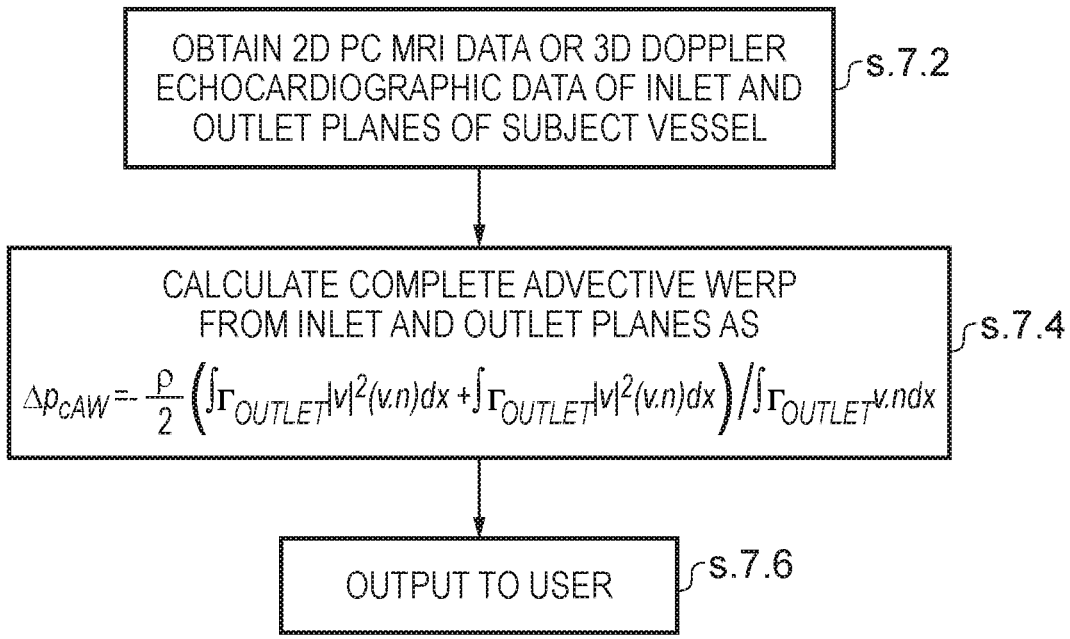
FIG. 7 is a flow diagram relating to the operation of a second embodiment of the invention.

FIG. 7 illustrates the basic method of operation of the cAW approach. Here, at s.7.2 the MRI data or ECG data of the inlet and outlet planes of the subject vessel for which pressure drop across is to be found is obtained. Then, from this data the complete advective WERP values for the inlet and outlet planes are found, for example using the processing represented by equation A.3 above (s.7.4). Finally the complete advective WERP data is stored and/or output to a user, for example on a display screen (s.7.6).

Third Embodiment: System Description

The third embodiment relates to the simplified advective WERP approach, which can be performed using 2D Doppler ECG data, although of course it may also be applied with other imaging systems that obtain more information, such as 2D PC MRI, 3D Doppler ECG. In this example, however, FIG. 10(B) shows a 2D Doppler ultrasound ECG equivalent system. Here a transducer 1000 obtains 2D Doppler measurements from the subject, under the control of 2D Doppler ECG system 152, comprising 2D Doppler ECG controller 154. The system produces 2D Doppler ECG data 156, and which is then used as an input to the sAW calculation program 158, which performs the necessary processing as described previously to find solutions for the outlet planes of the vessel being monitored, which is then stored and output as sAW output data 160.

Figure 8:
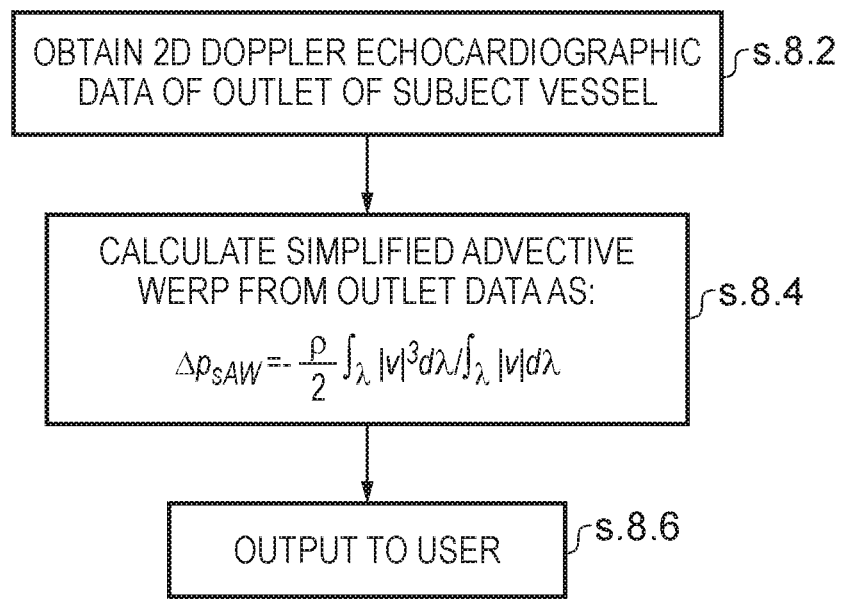
FIG. 8 is a flow diagram relating to the operation of a third embodiment of the invention.

FIG. 8 illustrates the basic method of operation of the sAW approach. Here, at s.8.2 the ECG data of the outlet plane of the subject vessel for which pressure drop across is to be found is obtained. Then, from this data the simplified advective WERP values for the inlet or outlet planes are found, for example using the processing represented by equation A.5 above (s.8.4). Finally the simplified advective WERP data is stored and/or output to a user, for example on a display screen (s.8.6).

For completeness, brief further description of the remaining figures is undertaken below.

FIG. 11 shows the TPD estimated from 4D PC-MRI data using the WERP formulation. Top panel: average temporal transients of the TPD during systole of the total (top left), kinetic (top right), advective (bottom left) and viscous (bottom right) components on Group I (light grey filled area) and Group II (dark grey filled area) subjects. Bottom panel: distribution (mean±standard deviation) for peak TPD $\Delta p_{MAX}$ (mmHg), including the significance of differences between Group I and Group II (unpaired T-test). Peak values of the kinetic pressure drops are reported on acceleration and deceleration (into brackets, negative peaks) systolic events separately. It must be noted that the pressure components do not add up to the total TPD, as the peak kinetic, advective and viscous drops do not happen simultaneously.

FIG. 12 shows correlations between mean TPD estimated from 4D PC-MRI data with cAW against sB (A), cB (B) and sAW (C) formulations. Case-specific values and regression line for Group I (blue) and Group II (red) subjects. Grey dashed line in (A) shows the mild-to-severe stenosis threshold defined as $\Delta p_{sB}=20$ mmHg (Baumgartner 2009) from the simplified Bernoulli formulation.

FIG. 13 shows the results of computation of WERP advective drops based on 4D PC-MRI and idealized echocardiographic data. (A) Systolic advective TPD transients computed from 4D PCMRI (black solid line), color Doppler 3D (grey solid line) using the sAW formulation, color Doppler 2D using the sAW formulation to 1D profiles obtained at the peak systolic frame (grey circles), and continuous Doppler 1D using the sB formulation (grey dashed line). (B) Linear regression and correlation factor between peak advective TPD computed from 4D PC-MRI and Doppler echocardiographic data: color Doppler 3D using the sAW formulation (solid blue line), color Doppler 2D using the sAW formulation to 1D profiles 2 (solid black line with errorbars for 12 sampled profiles) and Doppler 1D using the sB formulation (solid red line). Case-specific values are shown for each Doppler based acquisition technique.

FIG. 14 illustrates pressure drops in the AAR estimated from 4D PC-MRI data using the WERP formulation. Top panel: average temporal transients of the pressure drops during systole, with total (top left), kinetic (top right), advective (bottom left) and viscous (bottom right) components on Group I (light grey filled area) and Group II (dark grey filled area) subjects. Bottom panel: distribution (mean±standard deviation) for peak drops $\Delta p_{MAX}$(mmHg) including the significance of differences between Group I and Group II (unpaired T-test). Peak values of the kinetic pressure drops are reported on acceleration and deceleration (into brackets, negative peaks) systolic events separately.

FIG. 15 shows pressure drops in the DAR estimated from 4D PC-MRI data using the WERP formulation. Top panel: average temporal transients of the drops during systole, with total (top left), kinetic (top right), advective (bottom left) and viscous (bottom right) components on Group I (light grey filled area) and Group II (dark grey filled area) subjects. Bottom panel: distribution (mean±standard deviation) for peak drops $\Delta p_{MAX}$(mmHg), including the significance of differences between Group I and Group II (unpaired T-test). Peak values of the total and kinetic pressure drops are reported on acceleration and deceleration (into brackets) systolic events separately.

Figure 16:
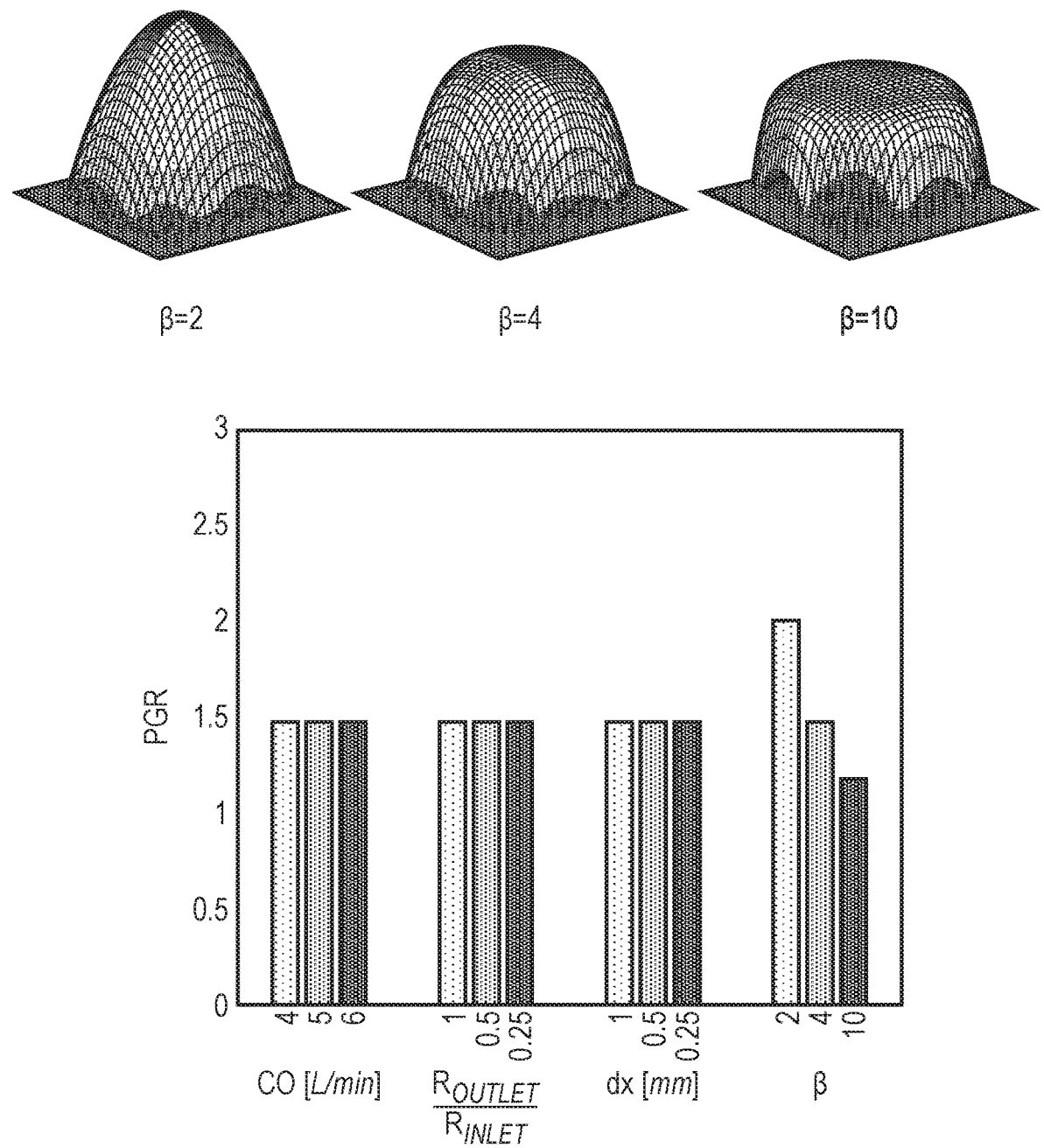

FIG. 16 shows the results of an in silico test on a 3D straight pipe with steady velocity field. Top panel: representation of velocity profiles at inlet/outlet planes obtained with different velocity shape coefficients. Bottom panel: pressure gradient ratio (PGR=$\Delta p_{cB}/\Delta p_{cAW}$) between drops estimated with cB and cAW formulations as a function of cardiac output outlet/inlet radii ratio $R_{OUTLET}/R_{INLET}$, spatial discretization dx and velocity shape coefficient β.

Figure 17B:
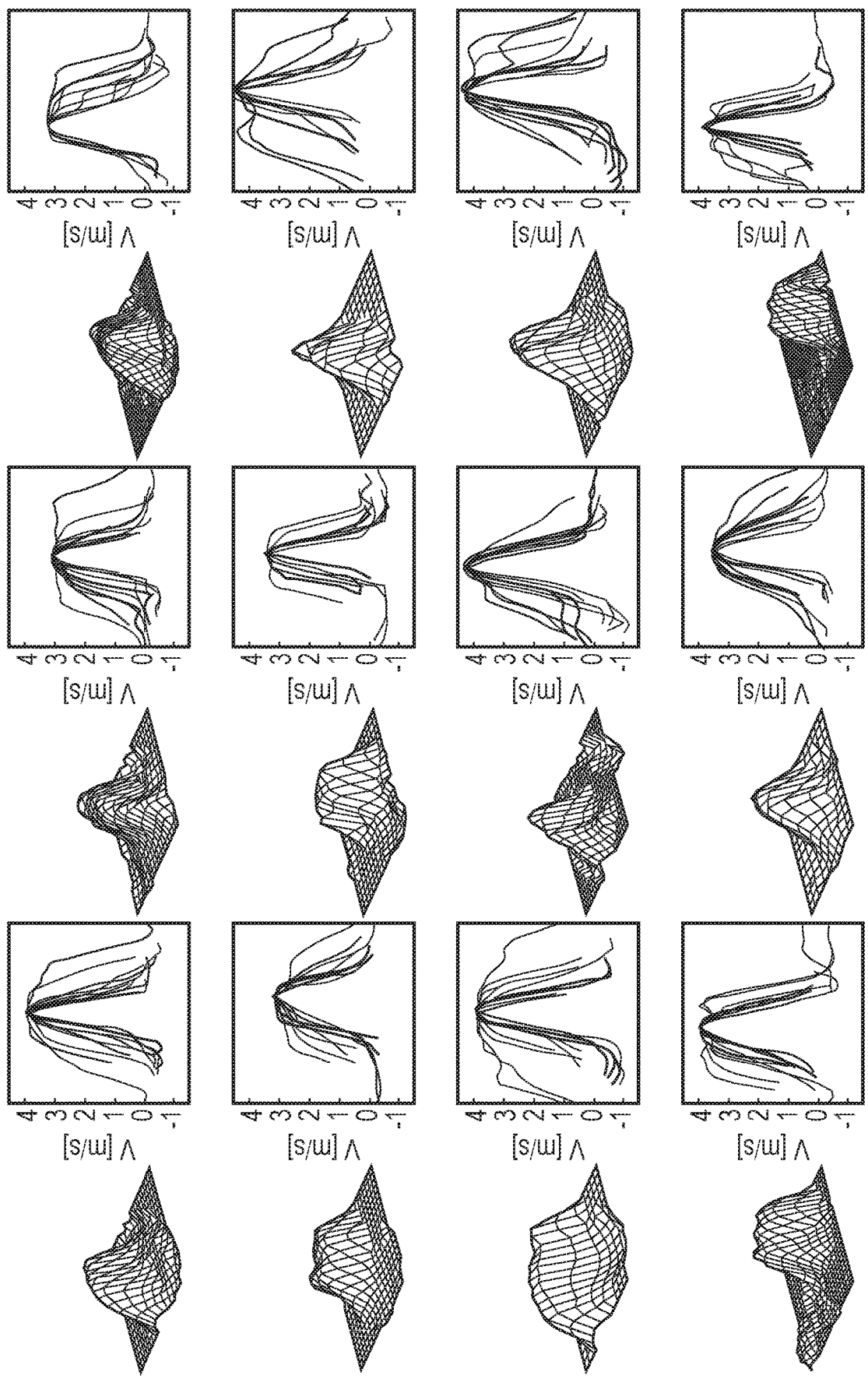

FIG. 17 shows 2D velocity profiles from mimicked 2D color Doppler echocardiographic images at the outlet plane for Group I (FIG. 17A) and Group II (FIG. 17B).

Various modifications to the above described embodiments, whether by way of addition, deletion or substitution, will be apparent to the skilled person to provide additional embodiments, any and all of which are intended to be encompassed by the appended claims.

REFERENCES

1. Cioffi G, Faggiano P, Vizzardi E, Tarantini L, Cramariuc D, Gerdts E, de Simone G. Prognostic effect of inappropriately high left ventricular mass in asymptomatic severe aortic stenosis. *Heart.* 2011; 97:301-307.
2. Otto C M. Valvular Aortic Stenosis. Disease Severity and Timing of Intervention. *J Am Coll Cardiol.* 2006; 47:2141-2151.
3. Minners J, Allgeier M, Gohlke-Baerwolf C, Kienzle R-P, Neumann F-J, Jander N. Inconsistencies of echocardiographic criteria for the grading of aortic valve stenosis. *Eur Heart J.* 2008; 29:1043-8.
4. Vahanian A, Alfieri O, Andreotti F, Antunes M J, Barón-Esquivias G, Baumgartner H, Borger M A, Carrel T P, De Bonis M, Evangelista A, Falk V, Jung B, Lancellotti P, Pierard L, Price S, Schäfers H-J, Schuler G, Stepinska J, Swedberg K, Takkenberg J, Von Oppell U O, Windecker S, Zamorano J L, Zembala M, Bax J J, Ceconi C, Dean V, Deaton C, Fagard R, Funck-Brentano C, Hasdai D, Hoes A, Kirchhof P, Knuuti J, Kolh P, McDonagh T, Moulin C, Popescu B A, Reiner, Sechtem U, Sirnes P A, Tendera M, Torbicki A, Von Segesser L, Badano L P, Bunc M, Claeys M J, Drinkovic N, Filippatos G, Habib G, Kappetein A P, Kassab R, Lip G Y H, Moat N, Nickenig G, Otto C M, Pepper J, Piazza N, Pieper P G, Rosenhek R, Shuka N, Schwammenthal E, Schwitter J, Mas P T, Trindade P T, Walther T. Guidelines on the management of valvular heart disease (version 2012). *Eur Heart J.* 2012; 33:2451-96.
5. Bach D S. Echo/Doppler evaluation of hemodynamics after aortic valve replacement: principles of interrogation and evaluation of high gradients. *JACC Cardiovasc Imaging.* 2010; 3:296-304.
6. Bahlmann E, Cramariuc D, Gerdts E, Gohlke-Baerwolf C, Nienaber C a., Eriksen E, Wachtell K, Chambers J, Kuck K H, Ray S. Impact of pressure recovery on echocardiographic assessment of asymptomatic aortic stenosis: A SEAS substudy. *JACC Cardiovasc Imaging.* 2010; 3:555-562.
7. Baumgartner H, Khan S, DeRobertis M, Czer L, Maurer G. Discrepancies between Doppler and catheter gradients in aortic prosthetic valves in vitro. A manifestation of localized gradients and pressure recovery. *Circulation.* 1990; 82:1467-1475.
8. Baumgartner H, Stefenelli T, Niederberger J, Schima H, Maurer G. "Overestimation" of catheter gradients by Doppler ultrasound in patients with aortic stenosis: A predictable manifestation of pressure recovery. *J Am Coll Cardiol.* 1999; 33:1655-1661.
9. Garcia D, Dumesnil J G, Durand L G, Kadem L, Pibarot P. Discrepancies between catheter and doppler estimates of valve effective orifice area can be predicted from the pressure recovery phenomenon: Practical implications with regard to quantification of aortic stenosis severity. *J Am Coll Cardiol.* 2003; 41:435-442.
10. Gardner R M. Direct arterial pressure monitoring. *Curr Anaesth Crit Care.* 1990; 1:239-246.
11. Niederberger J, Schima H, Maurer G, Baumgartner H. Importance of pressure recovery for the assessment of aortic stenosis by Doppler ultrasound. Role of aortic size, aortic valve area, and direction of the stenotic jet in vitro. *Circulation.* 1996; 94:1934-1940.
12. Baumgartner H, Hung J, Bermejo J, Chambers J B, Evangelista A, Griffin B P, Jung B, Otto C M, Pellikka P A, Quinones M. Echocardiographic assessment of valve stenosis: EAE/ASE recommendations for clinical practice. *J Am Soc Echocardiogr.* 2009; 22:1-23; 101-102.
13. Nishimura R a., Otto C M, Bonow R O, Carabello B a., Erwin J P, Guyton R a., O'Gara P T, Ruiz C E, Skubas N J, Sorajja P, Sundt T M, Thomas J D. 2014 AHA/ACC guideline for the management of patients with valvular heart disease: A report of the American college of cardiology/American heart association task force on practice guidelines. *J Am Coll Cardiol.* 2014; 63:e57-e185.
14. Markl M, Wallis W, Brendecke S, Simon J, Frydrychowicz A, Harloff A. Estimation of global aortic pulse wave velocity by flow-sensitive 4D MRI. *Magn Reson Med.* 2010; 63:1575-82.
15. Markl M, Kilner P J, Ebbers T. Comprehensive 4D velocity mapping of the heart and great vessels by cardiovascular magnetic resonance. *J Cardiovasc Magn Reson.* 2011; 13:7.
16. Stankovic Z, Allen B D, Garcia J, Jarvis K B, Markl M. 4D flow imaging with MRI. *Cardiovasc Diagn Ther.* 2014; 4:173-92.
17. Deng Z, Fan Z, Xie G, He Y, Natsuaki Y, Jin N, Bi X, An J, Liu X, Zhang Z, Fan Z, Li D. Pressure gradient measurement in the coronary artery using 4D PC-MRI: towards noninvasive quantification of fractional flow reserve. *J Cardiovasc Magn Reson.* 2014; 16:055.
18. Donati F, Nordsletten D A, Smith N P, Lamata P. Pressure Mapping from Flow Imaging: Enhancing Computation of the Viscous Term Through Velocity Reconstruction in Near-Wall Regions. In: EMBC, IEEE EMB. 2014.
19. Krittian S B S, Lamata P, Michler C, Nordsletten D a, Bock J, Bradley C P, Pitcher A, Kilner P J, Markl M, Smith N P. A finite-element approach to the direct computation of relative cardiovascular pressure from time-resolved MR velocity data. *Med Image Anal.* 2012; 16:1029-37.
20. Meier S, Hennemuth A, Friman O, Bock J, Markl M, Preusser T. Non-invasive 4D Blood Flow and Pressure Quantification in Central Blood Vessels via PC-MRI. 2010; 903-906.

21. Donati F, Figueroa C A, Smith N P, Lamata P, Nordsletten D A. Non-invasive pressure difference estimation from PC-MRI using the work-energy equation. *Med Image Anal.* 2015; 26:159-172.
22. Lamata P, Pitcher A, Krittian S, Nordsletten D, Bissell M M, Cassar T, Barker A J, Markl M, Neubauer S, Smith N P. Aortic relative pressure components derived from four-dimensional flow cardiovascular magnetic resonance. *Magn. Reson. Med.* 2013;
23. Baumgartner H, Hung J, Bermejo J, Chambers J B, Evangelista A, Griffin B P, Iung B, Otto C M, Pellikka P A, Quinones M. Echocardiographic assessment of valve stenosis: EAE/ASE recommendations for clinical practice. *Eur J Echocardiogr.* 2009; 10:1-25.
24. Chan R W, Von Deuster C, Giese D, Stoeck C T, Harmer J, Aitken A P, Atkinson D, Kozerke S. Characterization and correction of eddy-current artifacts in unipolar and bipolar diffusion sequences using magnetic field monitoring. *J Magn Reson.* 2014; 244:74-84.
25. Moussavi A, Untenberger M, Uecker M, Frahm J. Correction of gradient-induced phase errors in radial MRI. *Magn Reson Med.* 2014; 71:308-312.
26. Rohde G K, Barnett a. S, Basser P J, Marenco S, Pierpaoli C. Comprehensive Approach for Correction of Motion and Distortion in Diffusion-Weighted MRI. *Magn Reson Med.* 2004; 51:103-114.
27. Bock J, Frydrychowicz A, Lorenz R, Hirtler D, Barker A J, Johnson K M, Arnold R, Burkhardt H, Hennig J, Markl M. In vivo noninvasive 4D pressure difference mapping in the human aorta: phantom comparison and application in healthy volunteers and patients. *Magn Reson Med.* 2011; 66:1079-88.
28. Lee T C, Kashyap R L, Chu C N. Building Skeleton Models via 3-D Medial Surface Axis Thinning Algorithms. *CVGIP Graph. Model. Image Process.* 1994; 56:462-478.
29. Garcia J, Capoulade R, Le Ven F, Gaillard E, Kadem L, Pibarot P, Larose É. Discrepancies between cardiovascular magnetic resonance and Doppler echocardiography in the measurement of transvalvular gradient in aortic stenosis: the effect of flow vorticity. *J Cardiovasc Magn Reson.* 2013; 15:84.
30. Laske a, Jenni R, Maloigne M, Vassalli G, Bertel O, Turina M I. Pressure gradients across bileaflet aortic valves by direct measurement and echocardiography. *Ann Thorac Surg.* 1996; 61:48-57.
31. Zhang Y, Nitter-Hauge S. Determination of the mean pressure gradient in aortic stenosis by Doppler echocardiography. *Eur Heart J.* 1985; 6:999-1005.
32. Hatle L, Brubakk a, Tromsdal a, Angelsen B. Noninvasive assessment of pressure drop in mitral stenosis by Doppler ultrasound. *Br Heart J.* 1978; 40:131-40.
33. Chambers J B. Aortic stenosis. *Eur. J Echocardiogr.* 2009; 10:i11-i19.
34. Rijsterborgh H, Roelandt J. Doppler assessment of aortic stenosis: Bernoulli revisited. *Ultrasound Med Biol.* 1987; 13:241-248.
35. Scantlebury D C, Geske J B, Nishimura R a. Limitations of doppler echocardiography in the evaluation of serial stenoses. *Circ Cardiovasc Imaging.* 2013; 6:850-852.
36. Gersh B J, Maron B J, Bonow R O, Dearani J A, Fifer M A, Link M S, Naidu S S, Nishimura R A, Ommen S R, Rakowski H, Seidman C E, Towbin J A, Udelson J E, Yancy C W. 2011 ACCF/AHA Guideline for the Diagnosis and Treatment of Hypertrophic Cardiomyopathy: a report of the American College of Cardiology Foundation/American Heart Association Task Force on Practice Guidelines. Developed in collaboration with the American As. *J Am Coll Cardiol.* 2011; 58:e212-60.
37. Otto C, Burwash I, Legget M, Munt B, Fujioka M, Healy N, Kraft C, Miyake-Hull C, Schwaegler R. Prospective Study of Asymptomatic Valvular Aortic Stenosis. *Circulation.* 1997; 95:2262-70.
38. Bermejo J, Antoranz J C, Yotti R, Moreno M, Garcia-Fernandez M A. Spatio-temporal mapping of intracardiac pressure gradients. A solution to Euler's equation from digital postprocessing of color Doppler M-mode. *Ultrasound Med Biol.* 2001; 27:621-630.
39. Garcia D, Pibarot P, Durand L G. Analytical modeling of the instantaneous pressure gradient across the aortic valve. *J Biomech.* 2005; 38:1303-1311.
40. Heys J J, Holyoak N, Calleja A M, Belohlavek M, Chaliki H P. Revisiting the simplified bernoulli equation. *Open Biomed Eng J.* 2010; 4:123-8.
41. de Vecchi A, Clough R E, Gaddum N R, Rutten M C M, Lamata P, Schaeffter T, Nordsletten D a, Smith N P. Catheter-induced errors in pressure measurements in vessels: an in-vitro and numerical study. *IEEE Trans Biomed Eng.* 2014; 61:1844-50.
42. Falahatpisheh A, Rickers C, Gabbert D, Heng E L, Stalder A, Kramer H-H, Kilner P J, Kheradvar A. Simplified Bernoulli's method significantly underestimates pulmonary transvalvular pressure drop. *J Magn Reson Imaging.* 2015; n/an/a.

The invention claimed is:

1. A method of determining pressure difference across a tube arising from fluid flow within the tube, comprising:
   obtaining fluid velocity data at the inlet and outlet planes of the tube; and
   processing the fluid velocity data to determine:
   i) a flow rate (Q) of the fluid through the tube; and
   ii) an advective energy rate (A) of the fluid flow through the tube;
   the method further comprising calculating the pressure difference in dependence on both of the flow rate (Q), and the advective energy rate (A), without considering a viscous dissipation rate (V) and the kinetic energy (K) of the fluid flow through the tube;
   wherein the pressure difference across the tube is given by one of:

$$\Delta p_{cAW} = -\frac{\rho}{2}\left(\int_{\Gamma_{OUTLET}}|v|^2(v\cdot n)dx + \int_{\Gamma_{INLET}}|v|^2(v\cdot n)dx\right)\bigg/\int_{\Gamma_{OUTLET}}v\cdot n\,dx$$

where v is a velocity field at a generic voxel, n is the normal direction on inlet and outlet planes, rho is the fluid density respectively, and $\Gamma_{INLET}$ and $\Gamma_{OUTLET}$ are the respective inlet and outlet planes of the tube; or $$\Delta p_{sAW} = -\frac{\rho}{2}\int_{\Gamma_{OUTLET}}|v|^2(v\cdot n)dx\bigg/\int_{\Gamma_{OUTLET}}v\cdot n\,dx$$

where v is a velocity field at a generic voxel, rho is the fluid density respectively, $\Gamma_{OUTLET}$ is a selected plane of the tube, and n is the normal direction on the selected plane, wherein the selected plane is one of the planes at any end of the tube.

2. A method according to claim 1, wherein:
   a) the flow rate Q is dependent on a surface integral of the fluid velocity data across either the inlet or outlet plane of the tube, or across any other plane dividing the tube in two sub-sections; and/or b) the advective energy rate A is dependent on a sum of the surface integrals of the time dependent fluid velocity data, or data derived therefrom, across the inlet and outlet planes and the fluid density.

3. A method according to claim 1, wherein fluid velocity data is not obtained for anywhere else in the tube other than the inlet and outlet planes.

4. A method according to claim 1, wherein fluid velocity data is not obtained for anywhere else in the tube other than the selected plane.

5. A method according to claim 1, wherein the tube is a blood vessel, and the fluid flow is in vivo blood flow, and wherein the fluid velocity data is obtained from one of:
   i) 4D phase contrast magnetic resonance imaging data; and/or
   ii) 2D phase contrast magnetic resonance imaging data; and/or
   iii) Doppler echocardiographic data; and/or
   iv) Ultrafast echocardiographic data.

6. A method of determining a pressure difference across a tube arising from fluid flow within the tube, comprising:
   obtaining partial fluid velocity data from the outlet of the tube;
   estimating what a full velocity profile is from the partial fluid velocity data; and
   calculating the pressure difference in dependence on the partial fluid velocity data and a known fluid density;
   where the observation of data along a line is directly taken as the best estimation of the full velocity profile, and as such the pressure difference is given by:

$$\Delta p_{sAW} = -\frac{\rho}{2} \int_\lambda |v|^3 d\lambda \bigg/ \int_\lambda |v| d\lambda$$

where v is the fluid velocity along the line λ, and rho is the fluid density.

7. A method according to claim 6, wherein the partial data is acquired along a line at the outlet plane of the tube, the line being defined by intersecting an imaging plane with the outlet plane of the tube.

8. A method according to claim 6, wherein the data is not a 3D vector but is a projection of this vector in a direction close to the direction of the flow.

9. A method of determining pressure difference across a tube arising from fluid flow within the tube, comprising:
   obtaining partial fluid velocity data from the outlet of the tube;
   estimating what the full velocity profile is from the partial data; and
   calculating the pressure difference in dependence on the fluid velocity data and a known fluid density, where the full velocity profile is estimated as a circular profile divided in two axisymmetric parts, each of them as the extrapolation in the circumferential direction of the data along the observed line, and as such the pressure difference is given by:

$$\Delta p_{sAW} = -\frac{\rho}{2} \sum_{\lambda=0}^{\lambda=L} |v|^3 |\lambda - L/2| d\lambda \bigg/ \int_{\lambda=0}^{\lambda=L} |v| |\lambda - L/2| d\lambda$$

where v is the fluid velocity along the line λ of length L, and rho is the fluid density.

10. A method of determining a pressure difference across a tube arising from fluid flow within the tube, comprising:
    obtaining partial fluid velocity data from an outlet of the tube;
    estimating what a full velocity profile is from the partial fluid velocity data; and
    calculating the pressure difference in dependence on the partial fluid velocity data and a known fluid density, wherein:
    a) the partial fluid velocity data is acquired along several lines at an outlet plane of the tube, each line being defined by intersecting an imaging plane with the outlet plane of the tube; or
    b) the partial fluid velocity data is acquired at a sparse set of points or lines around the outlet plane, in such a manner that the velocity at the outlet plane can be inferred by interpolation or extrapolation, wherein the pressure difference is given by:

$$\Delta p_{sAW} = -\frac{\rho}{2} \int_{\Gamma_{OUTLET}} |v_R|^2 (v_R \cdot n) dx \bigg/ \int_{\Gamma_{OUTLET}} v_R \cdot n dx$$

where $v_R$ is the fluid velocity vector reconstructed from the acquired partial fluid velocity data, n is the normal direction on the outlet plane, $\Gamma_{OUTLET}$ is an outlet plane of the tube, and rho is the fluid density.

11. A method according to claim 6, wherein the tube is a blood vessel, and the fluid flow is in vivo or ex-vivo blood flow, and where the fluid velocity data is obtained by
    i) 2D Doppler echocardiography; and/or
    ii) ultrafast 2D echocardiography.

12. A method according to claim 6, wherein only partial fluid velocity data is obtained from the outlet of the tube, relating to only a portion of the outlet rather than fluid velocity data across the whole outlet.

13. A method of determining pressure difference across a tube arising from fluid flow within the tube, comprising:
    obtaining three-dimensional time dependent fluid velocity data at a plurality of points along the tube;
    segmenting a domain of interest in the tube for which flow information therethrough is desired;
    defining a flow vector field w through the segmented domain, being a field that is divergence free and that has null values in the lateral walls of the tube;
    processing the flow vector field w and the three-dimensional time dependent fluid velocity data to determine:
    i) a flow rate (Qw) of the flow vector field w;
    ii) a surrogate kinetic energy (Kw) of the fluid flow through the tube;
    iii) a surrogate advective energy rate (Aw) of the fluid flow through the tube; and
    iv) a surrogate viscous dissipation rate (Vw) pertaining to the fluid flow; and
    calculating the pressure difference in dependence on all of the flow rate (Qw), and surrogates of kinetic energy (Kw), advective energy rate (Aw), and viscous dissipation rate (Vw).

14. A method according to claim 13, wherein the flow rate Qw is dependent on a surface integral of the flow vector field w across either the inlet or outlet plane of the tube, or across any other plane dividing the tube in two sub-sections, or wherein the flow rate Qw is computed as a weighted average of aforementioned surface integrals.

15. A method according to claim 13, wherein the kinetic energy rate Kw is dependent on: the flow vector field w, the three dimensional time dependent fluid velocity data, and the fluid density.

16. A method according to claim 13, wherein the advective energy rate Aw is dependent on a sum of the surface integrals of the flow vector field w and of the three dimensional time dependent fluid velocity data, or data derived therefrom, across the inlet and outlet planes and the fluid density, or across all the external surfaces of the domain (inlet plane, outlet plane and lateral wall of the cylinder).

17. A method according to claim 13, wherein the viscous dissipation rate Vw is dependent on w, the three dimensional fluid velocity data and the fluid dynamic viscosity.

18. A method according to claim 13, wherein the fluid is blood, and the tube is a blood vessel, and wherein the three-dimensional time-dependent velocity data is obtained using 4D phase contrast magnetic resonance imaging or cardiac echocardiography through Doppler or by tracking contrast agents in ultrafast acquisitions.

19. A system for determining pressure difference across a tube arising from fluid flow within the tube, the system comprising one of the following
   a) a 4D phase contrast magnetic resonance imaging apparatus, arranged to collect three dimensional time dependent velocity data from across the tube, the system further comprising a processor arranged to perform the method of claim 13 to determine the pressure difference; or
   b) an echocardiographic imaging apparatus, arranged to collect three dimensional time dependent velocity data from across the tube, the system further comprising a processor arranged to reconstruct the velocity field from a collection of acquisitions, and to perform the method of claim 13 to determine the pressure difference.

* * * * *